US010072256B2

(12) United States Patent
Busse et al.

(10) Patent No.: US 10,072,256 B2
(45) Date of Patent: Sep. 11, 2018

(54) PROCESS FOR SEPARATING AND DETERMINING THE VIRAL LOAD IN A PANCREATIN SAMPLE

(75) Inventors: Frauke Busse, Hannover (DE); Martin Frink, Wedemark (DE); Dietmar Becher, Diedrichshagen (DE); Leopold Doehner, Greifswald (DE)

(73) Assignee: ABBOTT PRODUCTS GMBH, Hannover (DE)

( * ) Notice: Subject to any disclaimer, the term of this patent is extended or adjusted under 35 U.S.C. 154(b) by 509 days.

(21) Appl. No.: 11/751,497

(22) Filed: May 21, 2007

(65) Prior Publication Data
US 2008/0019959 A1 Jan. 24, 2008

Related U.S. Application Data

(60) Provisional application No. 60/747,891, filed on May 22, 2006.

(51) Int. Cl.
*C12N 9/94* (2006.01)
*A61K 38/54* (2006.01)
*C12N 7/02* (2006.01)
*A61K 38/00* (2006.01)

(52) U.S. Cl.
CPC .............. *C12N 9/94* (2013.01); *A61K 38/54* (2013.01); *A61K 38/00* (2013.01); *C12N 7/02* (2013.01)

(58) Field of Classification Search
CPC combination set(s) only.
See application file for complete search history.

(56) References Cited

U.S. PATENT DOCUMENTS

| | | | |
|---|---|---|---|
| 3,324,002 A | 6/1967 | Antonides | |
| 3,803,305 A | 4/1974 | Thuillier | |
| 3,950,508 A | 4/1976 | Mony et al. | |
| 3,956,483 A | 5/1976 | Lewis | |
| 3,986,927 A | 10/1976 | Melnick et al. | |
| 3,991,180 A | 11/1976 | Boettner et al. | |
| 4,019,958 A | 4/1977 | Hell et al. | |
| 4,079,125 A | 3/1978 | Sipos | |
| 4,106,991 A | 8/1978 | Markussen et al. | |
| 4,242,219 A | 12/1980 | Bogerman et al. | |
| 4,280,971 A | 7/1981 | Wischniewski et al. | |
| 4,447,412 A | 5/1984 | Bilton | |
| 4,490,361 A | 12/1984 | Heldebrant | |
| 4,533,562 A | 8/1985 | Ikegami et al. | |
| 4,623,624 A | 11/1986 | Schultze | |
| 4,689,297 A | 8/1987 | Good et al. | |
| 4,775,536 A | 10/1988 | Patell | |
| 4,786,505 A | 11/1988 | Lovgren et al. | |
| 4,929,774 A | 5/1990 | Fukamachi et al. | |
| 5,068,110 A | 11/1991 | Fawzi et al. | |
| 5,219,572 A | 6/1993 | Sivaramakrishman et al. | |
| 5,225,202 A | 7/1993 | Hodges et al. | |
| 5,260,074 A | 11/1993 | Sipos | |
| 5,300,433 A * | 4/1994 | Hrinda et al. | 435/238 |
| 5,302,400 A | 4/1994 | Sipos | |
| 5,324,649 A | 6/1994 | Arnold et al. | |
| 5,374,657 A | 12/1994 | Kyle | |
| 5,378,462 A | 1/1995 | Boedecker et al. | |
| 5,489,530 A | 2/1996 | Braatz et al. | |
| 5,536,661 A | 7/1996 | Boel et al. | |
| 5,570,104 A | 10/1996 | Hayashi | |
| 5,614,189 A | 3/1997 | Huge-Jensen | |
| 5,618,710 A | 4/1997 | Navia et al. | |
| 5,645,832 A | 7/1997 | Braatz et al. | |
| 5,658,871 A | 8/1997 | Batenburg et al. | |
| 5,719,115 A | 2/1998 | Paatz et al. | |
| 5,725,880 A | 3/1998 | Hirakawa et al. | |
| 5,750,104 A | 5/1998 | Sipos | |
| 5,750,148 A | 5/1998 | Maruyama et al. | |
| 5,766,912 A | 6/1998 | Boel et al. | |
| 5,783,545 A | 7/1998 | Paatz et al. | |
| 5,801,022 A | 9/1998 | Navia et al. | |
| 5,849,296 A | 12/1998 | Navia et al. | |
| 5,863,759 A | 1/1999 | Boel et al. | |
| 5,869,438 A | 2/1999 | Svendsen et al. | |
| 5,874,558 A | 2/1999 | Boel et al. | |
| 5,879,920 A | 3/1999 | Dale et al. | |
| 5,976,529 A | 11/1999 | Navia et al. | |
| 5,993,806 A | 11/1999 | Galle | |
| 6,004,768 A | 12/1999 | Navia et al. | |
| 6,011,001 A | 1/2000 | Navia et al. | |
| 6,025,391 A | 2/2000 | Haeberlin et al. | |
| 6,030,798 A | 2/2000 | Braatz et al. | |
| 6,051,220 A | 4/2000 | Scharpe | |

(Continued)

FOREIGN PATENT DOCUMENTS

CA 2263703 A1 8/1999
DE 2035739 A1 1/1972

(Continued)

OTHER PUBLICATIONS

Nilsson et al. Biosynthesis and morphogenesis of group C rotavirus in swine testicular cells. Arch. Virol. 1993, 133:21-37.*
Estes et al. Proteolytic enhancement of rotavirus infectivity: molecular mechanisms. J. Virol. 1981, p. 879-888.*
Wallis et al. Plaque enhancement of enteroviruses by magnesium chloride, cysteine and pancreatin. J. Bacteriol. 1966. vol. 91(5): 1932-1935.*
Fang et al. 1989. Purification and Characterization of Adult Diarrhea Rotavirus: Identification of Viral Structural Proteins. Journal of Virology, vol. 63, No. 5, p. 2191-2197.*
Sanekata et al. 1996. Isolation of Group B Porcine Rotavirus in Cell Culture. Journal of Clinical Microbiology, vol. 34, No. 3, p. 759-761.*
Villegas et al. A rapid method to produce high yields of purified rotavirus particles. Journal of Virological Methods 104 (2002) 9-19.*
McLean et al. (2000). Contamination detection in animal cell culture. Encyclopedia of Cell Technology edited by Spier, Raymond E, vols. 1-2. John Wiley & Sons. p. 586-598.*

(Continued)

*Primary Examiner* — Taeyoon Kim
(74) *Attorney, Agent, or Firm* — Neal, Gerber & Eisenberg LLP

(57) ABSTRACT

Processes for separating an infectious viral load from a pancreatin sample and for quantitatively determining the viral load in a pancreatin sample are described herein.

14 Claims, No Drawings

(56) References Cited

U.S. PATENT DOCUMENTS

| | | | |
|---|---|---|---|
| 6,054,136 | A | 4/2000 | Farah et al. |
| 6,140,475 | A | 10/2000 | Margolin et al. |
| 6,187,572 | B1 | 2/2001 | Platz et al. |
| 6,224,910 | B1 | 5/2001 | Ullah et al. |
| 6,267,985 | B1 | 7/2001 | Chen et al. |
| 6,278,794 | B1 | 8/2001 | Parekh et al. |
| 6,312,704 | B1 | 11/2001 | Farah et al. |
| 6,348,442 | B2 | 2/2002 | Markussen |
| 6,355,461 | B2 | 3/2002 | Henriksen et al. |
| 6,426,091 | B1 | 7/2002 | Okumura et al. |
| 6,692,771 | B2 | 2/2004 | Pather et al. |
| 6,734,188 | B1 | 5/2004 | Rhodes et al. |
| 6,749,851 | B2 | 6/2004 | Mann et al. |
| 6,767,729 | B1 | 7/2004 | Nagano et al. |
| 7,211,281 | B2 | 5/2007 | Van Beek et al. |
| 7,479,378 | B2 | 1/2009 | Potthoff et al. |
| 7,658,918 | B1 | 2/2010 | Ortenzi |
| 8,221,747 | B2 | 7/2012 | Ortenzi |
| 8,246,950 | B2 | 8/2012 | Ortenzi |
| 2001/0046493 | A1 | 11/2001 | Margolin et al. |
| 2002/0061302 | A1 | 5/2002 | Sander-Struckmeier et al. |
| 2002/0137156 | A1 | 9/2002 | Margolin et al. |
| 2002/0146451 | A1 | 10/2002 | Sharma et al. |
| 2003/0007962 | A1 | 1/2003 | Vergez et al. |
| 2003/0017144 | A1 | 1/2003 | Margolin et al. |
| 2003/0021844 | A1 | 1/2003 | Barthelemy et al. |
| 2003/0049245 | A1 | 3/2003 | Mann et al. |
| 2003/0086948 | A1 | 5/2003 | Benameur et al. |
| 2003/0104048 | A1 | 6/2003 | Petal et al. |
| 2003/0175259 | A1 | 9/2003 | Karageozian et al. |
| 2003/0180352 | A1 | 9/2003 | Patel et al. |
| 2003/0211127 | A1 | 11/2003 | Margolin et al. |
| 2004/0013697 | A1 | 1/2004 | Berndl et al. |
| 2004/0033220 | A1 | 2/2004 | Hartmann |
| 2004/0057944 | A1 | 3/2004 | Galle et al. |
| 2004/0101562 | A1 | 5/2004 | Maio |
| 2004/0161423 | A1 | 8/2004 | Kumar |
| 2004/0202643 | A1 | 10/2004 | Margolin et al. |
| 2004/0213847 | A1 | 10/2004 | Matharu et al. |
| 2005/0250817 | A1 | 11/2005 | Shlieout |
| 2005/0250935 | A1* | 11/2005 | Dattilo .................. C07K 14/59 530/397 |
| 2007/0148151 | A1* | 6/2007 | Frink et al. .................. 424/94.3 |
| 2007/0148152 | A1 | 6/2007 | Shlieout et al. |
| 2007/0148153 | A1 | 6/2007 | Shlieout |
| 2007/0178120 | A1 | 8/2007 | Morrison et al. |
| 2008/0019959 | A1 | 1/2008 | Becher et al. |
| 2008/0292610 | A1 | 11/2008 | Hartmann |
| 2009/0130063 | A1 | 11/2008 | Singh |
| 2009/0226414 | A1 | 9/2009 | Tijssen et al. |

FOREIGN PATENT DOCUMENTS

| | | | |
|---|---|---|---|
| DE | 2410241 | A1 | 9/1975 |
| DE | 2512746 | A1 | 9/1976 |
| DE | 2626109 | A1 | 12/1976 |
| DE | 2923279 | C2 | 11/1980 |
| DE | 3642853 | A1 | 6/1988 |
| DE | 4203315 | A1 | 8/1992 |
| DE | 4200002 | | 7/1993 |
| DE | 4322229 | A1 | 1/1995 |
| DE | 4344215 | A1 | 6/1995 |
| DE | 19907764 | A1 | 11/1999 |
| DE | 19848849 | A1 | 4/2000 |
| DE | 19856415 | A1 | 6/2000 |
| DE | 10012095 | A1 | 9/2000 |
| DE | 29824797 | U1 | 8/2002 |
| EP | 0008780 | A2 | 3/1980 |
| EP | 0019253 | A1 | 11/1980 |
| EP | 0021129 | A2 | 1/1981 |
| EP | 0035780 | A1 | 9/1981 |
| EP | 0141607 | A2 | 5/1985 |
| EP | 0170360 | A1 | 2/1986 |
| EP | 0193829 | A2 | 9/1986 |
| EP | 0206417 | A2 | 12/1986 |
| EP | 0238023 | | 9/1987 |
| EP | 0304331 | A2 | 2/1989 |
| EP | 0304332 | A2 | 2/1989 |
| EP | 0305216 | | 3/1989 |
| EP | 0326026 | B1 | 8/1989 |
| EP | 0458845 | A1 | 8/1990 |
| EP | 0458849 | A1 | 8/1990 |
| EP | 0407225 | A1 | 1/1991 |
| EP | 0600868 | A1 | 12/1991 |
| EP | 0550450 | A1 | 2/1992 |
| EP | 0592478 | A1 | 1/1993 |
| EP | 0583726 | A2 | 2/1994 |
| EP | 0691982 | B1 | 1/1996 |
| EP | 0828509 | A1 | 12/1996 |
| EP | 0826375 | B1 | 3/1998 |
| EP | 0973878 | A1 | 10/1998 |
| EP | 0897985 | A2 | 2/1999 |
| EP | 1010423 | A2 | 6/2000 |
| EP | 1138333 | B1 | 4/2001 |
| EP | 1186658 | | 3/2002 |
| EP | 1261368 | A2 | 12/2002 |
| EP | 1279402 | A1 | 1/2003 |
| EP | 05107472 | | 8/2005 |
| EP | 05107474 | | 8/2005 |
| EP | 1593688 | | 9/2005 |
| EP | 1 593 688 | | 11/2005 |
| EP | 2278002 | | 1/2011 |
| FR | 2313916 | A1 | 1/1977 |
| GB | 1509866 | | 5/1978 |
| JP | 04936885 | A | 4/1974 |
| JP | 58148814 | A | 9/1983 |
| JP | 58179492 | | 10/1983 |
| JP | 59169491 | A | 9/1984 |
| JP | 61162185 | | 7/1986 |
| JP | 62-029950 | | 2/1987 |
| JP | 04023991 | | 1/1992 |
| JP | 4023991 | | 1/1992 |
| JP | 4187085 | A | 7/1992 |
| JP | 8143457 | A | 6/1996 |
| JP | 09125096 | A | 5/1997 |
| WO | WO 82/03871 | | 11/1982 |
| WO | 1987/07292 | A1 | 12/1987 |
| WO | 1989/08694 | A1 | 9/1989 |
| WO | 1989/08695 | A1 | 9/1989 |
| WO | 1991/06638 | A1 | 5/1991 |
| WO | 91/07948 | | 6/1991 |
| WO | 91/014454 | A1 | 10/1991 |
| WO | 91/16060 | | 10/1991 |
| WO | WO 1991/16060 | | 10/1991 |
| WO | WO 91/18623 | | 12/1991 |
| WO | WO 92/02617 | | 2/1992 |
| WO | 1992/12645 | A1 | 8/1992 |
| WO | 1992/13030 | A1 | 8/1992 |
| WO | WO 93/00924 | | 1/1993 |
| WO | 1993/07260 | A1 | 4/1993 |
| WO | 1993/07263 | A1 | 4/1993 |
| WO | 93/18790 | | 9/1993 |
| WO | WO 94/08603 | | 4/1994 |
| WO | WO 95/07688 | | 3/1995 |
| WO | WO 95/08983 | | 4/1995 |
| WO | 95/15681 | | 6/1995 |
| WO | WO 95/15681 | | 6/1995 |
| WO | WO 1995/15681 | | 6/1995 |
| WO | 1995/22625 | A1 | 8/1995 |
| WO | 96/038170 | A1 | 12/1995 |
| WO | 1996/00343 | A1 | 1/1996 |
| WO | 1996/16151 | A1 | 5/1996 |
| WO | 1996/38527 | A1 | 12/1996 |
| WO | 1997/23605 | A1 | 7/1997 |
| WO | 1997/39116 | A1 | 10/1997 |
| WO | WO 97/42980 | | 11/1997 |
| WO | WO 98/00169 | | 1/1998 |
| WO | 98/38292 | | 9/1998 |
| WO | WO 1998/38292 | | 9/1998 |
| WO | WO 98/46732 | | 10/1998 |
| WO | WO 98/52561 | | 11/1998 |
| WO | WO 99/20745 | | 4/1999 |
| WO | WO 99/28344 | | 6/1999 |

(56) References Cited

FOREIGN PATENT DOCUMENTS

| WO | 99/044589 A1 | 9/1999 |
|---|---|---|
| WO | 2000/01793 A1 | 1/2000 |
| WO | 00/34510 | 6/2000 |
| WO | WO 2000/34510 | 6/2000 |
| WO | WO 00/54799 | 9/2000 |
| WO | WO 01/01960 | 1/2001 |
| WO | 2001/25412 A1 | 4/2001 |
| WO | 01/037808 A1 | 5/2001 |
| WO | 2001/58276 A2 | 8/2001 |
| WO | WO 01/68139 | 9/2001 |
| WO | 2002/20746 A1 | 3/2002 |
| WO | 2002/28369 A1 | 4/2002 |
| WO | 02/040045 A3 | 5/2002 |
| WO | WO 02/36156 | 5/2002 |
| WO | 02/060474 A2 | 8/2002 |
| WO | WO 03/047595 | 6/2003 |
| WO | 2003/055967 A1 | 7/2003 |
| WO | 2003/080827 A2 | 10/2003 |
| WO | WO 2004/007707 | 1/2004 |
| WO | 2004/069872 A1 | 8/2004 |
| WO | WO 2005/012911 | 2/2005 |
| WO | 2005/070962 A1 | 8/2005 |
| WO | WO 2005/092370 | 10/2005 |
| WO | 2006/044529 A1 | 4/2006 |
| WO | 2006/136159 A2 | 12/2006 |
| WO | 07/014896 A1 | 2/2007 |
| WO | 2007/020260 A2 | 2/2007 |
| WO | 2007020259 | 2/2007 |
| WO | 07/135125 A1 | 11/2007 |
| WO | 2008/079685 A2 | 7/2008 |

OTHER PUBLICATIONS

Brewer et al. Porcine Encephalomyocarditis Virus Persists in Pig Myocardium and Infects Human Myocardial Cells. J. Virology. 2001. p. 11621-11629.*
Sottong et al. Recovery of Murine Leukemia Virus from Large Volumes of Freshly Harvested Culture Fluids by Using a Single Density Gradient. Applied Microbiology, Jan. 1975, p. 102-105.*
CPMP. Note for Guidance on virus validation studies: The design, contrigution and interpretation of sutides validating the inactivation and removal of viruses. 1996. p. 1-13.*
Spearman, C., The method of 'right and wrong cases' ('constant stimuli') without Gauss's formulae, Brit. J. of Psych, vol. II, Part 3 (1908) 227-242.
Reed L. J. et al., A simple method of estimating fifty per cent endpoints, Amer. J. of Hygiene, vol. 27, No. 3 (May 1938) 493-497.
Tischer, I. et al., Replication of porcine circovirus: induction by glucosamine and cell cycle dependence, Arch. Virol (1987) 96: 39-57.
Lebowitz, J. et al., Modern analytical ultracentrifugation in protein science: A tutorial review, Protein Science (2002), 11: 2067-2079.
European Search Report and Preliminary Opinion for European Patent Application EP 06 11 4329, dated Aug. 1, 2006.
2.9.1 Disintegration of Tablets and Capsules, European Pharmacopoeia 5.3, pp. 3351-3353.
21 C.F.R. 201.302 Notice to manufacturers, packers, and distributors of drugs for internal use which contain mineral oil.
Chemical Abstract, No. 99:200535j, "Capsules Containing Stable Digestive Enzymes", vol. 99, p. 342 (1983).
Committee for Proprietary Medicinal Products, "Note for Guidance on Virus Validation Studies: The Design, Contribution and Interpretation of Studies Validating the Inactivation and Removal of Viruses," The European Agency for the Evaluation of Medicinal Products, pp. 1-3, Feb. 14, 1996.
D'Costa, D., "Diabetic Neuropathic Cachexia Associated with Malabsorption," Diabetic Medicine, vol. 9/2, pp. 203-205 (1992).
Delhaye, M., "Comparative Evaluation of a High Lipase Pancreatic Enzyme Preparation and a Standard Pancreatic Supplement for Treating Exocrine Pancreatic Insufficiency in Chronic Pancreatitis," European Journal of Gastroenterology and Hepatology, vol. 8/7, pp. 699-703 (1996).

European Search Report for European Patent Application No. EP93112848 (dated Apr. 15, 1994).
European Search Report for European Patent Application No. EP 05733481.5 (dated Oct. 1, 2007).
Fiedler, Herbert P. (Lexikon der Hilfsstoffe fuer Pharmazie, Kosmetik und Angrenzende Gebiete, 5 Aufli. 2002), Encyclopedia of Excipients for Pharmaceuticals, Cosmetics and Related Areas, vol. 5, pp. 733 and 995, including English translation (cover page, pp. 747 & 921) (Total: Six (6) pages). Printed and bound by R. Oldenbourg Graphische Betriebe Druckerel GmbH, Kirchheim, Germany.
Guidance for Industry SUPAC-MR, Modified Release Solid Oral Doage Form, pp. 1-36 (Sep. 1997).
ICH Harmonised Tripartite Guideline, Table of Content and pp. 1-16.
International Preliminary Report of Patentability for PCT/EP2006/064717 (dated Oct. 11, 2007).
International Preliminary Report of Patentability for PCT/EP2006/065311 (dated Feb. 20, 2008).
International Preliminary Report of Patentability for PCT/EP2006/065313 (dated Feb. 20, 2008).
International Preliminary Report of Patentability for PCT/EP2007/054880 (dated Nov. 27, 2008).
International Search Report for PCT/EP2000/002261 (dated Jul. 11, 2000).
International Search Report and Written Opinion for PCT/EP2006/064717 (dated Nov. 20, 2006).
International Search Report and Written Opinion for PCT/EP2006/065311 (dated Feb. 2, 2007).
International Search Report and Written Opinion for PCT/EP2006/065313 (dated Feb. 2, 2007).
Nakamura, et al., Pancreas, vol. 16(3), pp. 329-336.
"Pancreatin", The American Heritage Dictionary of the English Language, 4th Edition Boston, Houghton Mifflin (2002). www.bartleby.com/61/ (printed Mar. 21, 2007).
"Pancreatin juice", The American Heritage Dictionary of the English Language, 4th Edition Boston, Houghton Mifflin (2002). www.bartleby.com/61/ (printed Mar. 21, 2007).
Simek, I., "Substitution Therapy in Insufficient External Pancreatic Secretion," Online Medline Databse (1993).
Subramanian et al., "Effect of lipid excipients on in vitro pancreatic lipase activity," Drug Dev. Ind. Pharm., vol. 29(8), pp. 885-890 (2003).
Thomson et al., Porcine Parvovirus Infection, Infectious Disease of Livestock, vol. 2, Ch. 73, (2nd edition), pp. 806-814 (2004).
Turner, et al., "The Inactivation of Viruses in Pig Slurries: A Review," Bioresource Technology, vol. 61, pp. 9-20 (1997).
Ullman's Encyclopedia, pp. 175-176, 179, 180, and 199.
United States Pharmacopoeia for Pancrelipase Delayed-Release Capsules (2 pages).
United States Pharmacopoeia Method 711 Dissolution (18 pages).
International Search Report for PCT/EP2007/054880, dated Sep. 18, 2007.
Written Opinion of the International Searching Authority for PCT/EP2007/054880, dated Sep. 18, 2007.
European Search Report and Preliminary Opinion for European Patent Application No. 07120740.1, dated Mar. 3, 2008.
Spearman, The Method of 'Right and Wrong Cases' ('Constant Stimuli') Without Gauss's Formulae, The British Journal of Psychology, vol. 2, Part 3 (Jan. 1908) p. 227-242.
Tischer et al., Replication of porcine circovirus: induction by glucosamine and cell cycle dependence, Archives of Virology, vol. 96 (1987) p. 39-57.
Lebowitz et al., Modern analytical ultracentrifugation in protein science: A tutorial review, Protein Science, vol. 11 (2002) p. 2067-2079.
Reed et al., A Simple Method of Estimating Fifty Per Cent Endpoints, The American Journal of Hygiene, vol. 27, No. 3 (May 1938) p. 493-497.
English Abstract of JP 4023991.
Eurand S.A., Notice of Opposition against the European Patent No. EP 1931317., Sep. 23, 2009.
McGinity, Aqueous Polymeric Coatings for Pharmaceutical Dosage, Marcel Dekker, Inc., 1989.

(56) References Cited

OTHER PUBLICATIONS

Murthy, et al., "In Vitro Release Characteristics of Hard Shell Capsule Products Coated with Aqueous- and Organic-Based Enteric Polymers," Journal of Biomaterials Application, J. Biomater Appl., vol. 3, pp. 52-79 (1988).

Nordmark Arzneimittel GmbH & Co. KG, Notice of Opposition against the European Patent No. EP 1931317., Aug. 6, 2009 with translation.

Oshima, et al., "Preparation of Rapidly Disintegrating Tablets Containing Itraconazole Solids Dispersion," Chem. Pharm. Bull., vol. 55(11), pp. 1557-1562 (2007).

Reynolds, "A New Technique for the Production of Spherical Particles," Manufact. Chemist & Aerosol News, pp. 40-43 (Jun. 1970).

Sucker et al., "Pharmazeutische Techologie," pp. 273-283 (1991) with translation.

USP 32, NF 27, "Pancrelipase Delayed-Release Capsules." (2009) p. 3198.

Jiang et al., "Biochemical Characterization of the Structural and Nonstructural Polypeptides of a Porcine Group C Rotavirus," Journal of Virology, vol. 64(7), pp. 3171-3178 (1990).

Saif et al., "Serial Propagation of Porcine Group C Rotavirus (Pararotavirus) in a Continuous Cell Line and Characterization of the Passaged Virus," Journal of Clinical Microbiology, vol. 26(7), pp. 1277-1282 (1988).

Archibald, A.L., "Comparison of the Serum Amylases of Farm Animals," Comp. Biochem. Physiol., vol. 88B (3), pp. 963-968 (1987).

Cunningham, L. "Reactivation of Diethyl p-Nitrophenyl Phosphate-Inhibited α-Chymotrypsin by Hydroxylamine," Journal of Biological Chemistry, vol. 207, pp. 443-458 (1954).

Kobayashi, et al., "Susceptibility of Heptitis B Virus to Disinfectants or Heat," Journal of Clinical Microbiology, vol. 20 (2), pp. 214-216 (1984).

Maunula, L. "Molecular Epidemiology of Human Rotaviruses—A Study in Genetic Diversity," Academic Dissertation, Haartman Institute, pp. 1-116, Helsinki 2001.

Material Safety Data Sheet, Pancreatin 4X USP (10X), Invitrogen Corp., pp. 1-7 (Rev. Apr. 16, 2005).

Michen, et al., "Isoelectric Points of Viruses," Journal of Applied Microbiology, vol. 109, pp. 388-397 (2010).

Notice of Opposition, EP1931316, Eurand S.p.A, Nov. 15, 2010 (12 pages).

Sofer, et al., "Part 6, Inactiviation Methods Grouped by Virus," BioPharm Internationals, S-37-42 (2003).

Tsunemitsu, et al., "Isolation, Characterization, and Serial Propagation of a Bovine Group C Rotavirus in a Monkey Kidney cell Line (MA104)," Journal of Clinical Microbiology, vol. 29(11), pp. 2609-2613 (1991).

Walsh, et al., "Tryosinogen and Chymotrypsinogen as Homologous Proteins," PNAS, vol. 52, pp. 884-889 (1964).

Worthington Enzyme Manual, Lipase, (1993), pp. available at http://www.worthington-biochem.com/PL/default.html (2 pages).

Worthington Enzyme Manual, Trypsin (1993), available at http://www.worthington-biochem.com/TRY/default.html (3 pages).

Worthington Enzyme Manual, Trypsinogen (1993), available at http://www.worthington-biochem.com/TG/default.html (1 page).

Aquacoat ECD—FMC Biopolymer—Bulletin AECD-30-05/18/97. RS (1997).

Carriere, et al., "Quantitative Study of Digestive Enzyme Secretion and Gastrointestinal Lipolysis in Chronic Pancreatitis," Clinical Gastroenterology and Hepatology, vol. 3(1), pp. 28-38 (2005).

De Fiebre et al. "Elimination of *Salmonellae* from Animal Glandular Products," Applied Microbiology, vol. 17(3), pp. 344-346 (1969).

Delchier, et al., "Fate of Orally Ingested Enzymes in Pancreatic Insufficiency: Comparison of Two Pancreatic Enzyme Preparations," Aliment. Pharmacol. Therap., vol. 5, pp. 365-378 (1991).

Dimagno, et al., "Fate of Orally Ingested Enzymes in Pancreatic Insufficiency," The New England Journal of Medicine, vol. 296(23), pp. 1318-1322 (1977).

Dutta, et al., "Critical Examination of Therapeutic Efficacy of a pH-Sensitive Enteric-Coated Pancreatic Enzyme Preparation inTreatment of Exocrine Pancreatic Insufficiency Secondary to Cystic Fibrosis," Digestive Diseases and Sciences, vol. 33(10), pp. 1237-1244 (1988).

Enzyme Nomenclature., Recommendations of the Nomenclature Committee of the International Union of Biochemistry and Molecular Biology on the Nomenclature and Classification of Enzymes by the Reactions they Catalyse, available at http://www.chem.qmul.ac.uk/iubmb/enzyme/.

English Abstract of JP 4187085.

European Patent Appl. No. 06778012.2 Office Action dated Dec. 7, 2010 (5 pages).

Federal Register, vol. 69(82), Part IV, Apr. 28, 2004.

Fiedler, Herbert P. Encyclopedia of Excipients for Pharmaceuticals, Cosmetics and Related Areas, 5th ed., pp. 1284-1287 (2002).

Gregory, P.C., "Gastrointestinal pH, Motility/Transit and Permeability in Cystic Fibrosis," J Pediatr Gastroenterol Nutr, vol. 23(5), pp. 513-523 (1996).

Guarner, et al., "Fate of Oral Enzymes in Pancreatic Insufficiency," Gut, vol. 34, pp. 708-712 (1993).

Hogan et al., Pharmaceutical Coating Technology, Chapter 14, pp. 409-439 (1995).

International Preliminary Report of Patentability for PCT/EP2008/065586 (dated May 18, 2010).

International Search Report for PCT/EP2008/065586 (dated Dec. 19, 2008).

International Search Report PCT/EP2009/050010 (dated May 7, 2009).

Keller, et al., "Pancreatic Enzyme Supplementation Therpay," Current Treatment Option in Gastroenterology, vol. 6, pp. 369-374 (2003).

Keller, et al., "Human Pancreatic Exocrine Response to Nutrients in Health and Disease," Gut, vol. 54(Suppl. VI), pp. vi1-vi28 (2005).

Kreon® 25000 (magnified photograph).

Kreon® 25000 Gebrauchsinformation (2007), English Translation.

Layer, et al., "Fate of Pancreatic Enzymes During Small Intestinal Aboral Transit in Humans," The American Physiology Society, pp. G475-G480 (1986).

Layer, et al., "Pancreatic Enzymes in Chronic Pancreatitis," International Journal of Pancreatology, Col. 15(1), pp. 1-11 (1994).

Naftifine HCI MSDS (Jun. 23, 2004), available at http://pharmacycide.com/msds/Naftifine_HCL.

Pharmaceutical Excipients, 5th ed., Cetyl Alcohol, pp. 155-156 (2006).

Remington, The Science and Practice of Pharmacy, 20th ed., pp. 326 and 1035-1036 (2000).

Sachs-Barrable, et al., "Lipid Excipients Peceol and Gelucire 44/14 Decrease P-Glycoprotein Mediated Efflux of Rhodamine 123 Partially Due to Modifying P-Glycoprotein Protein Expression within Caco-2 Cells," J Pharm Pharmaceut Sci, vol. 10(3), pp. 319-331 (2007).

Savage et al., "Determination of Adequate Moisture Content for Efficient Dry-Heat Viral Inactivation in Lyophilized Factor VIII Loss on Drying and by Near Infrared Spectroscopy," Biologicals, vol. 26, pp. 119-124 (1998).

Sun et al., "Fluidized-bed spray coated porous hydrogel beads for sustained release of diclofenac sodium," Journal of Controlled Release, vol. 47, pp. 247-260 (1997).

The Ministry of Health, Labour and Welfare Ministerial Notification No. 285, Japan Pharmacopoeia, 8 pages (2006).

Thoma et al., "Influence of aqueous coatings on the stability of enteric coated pellets and tablets," European Journal of Pharmaceutics and Biopharmaceutics, vol. 47, pp. 39-50 A286(1999).

U.S. Appl. No. 12/271,480, filed May 21, 2007, Aug. 6, 2010 Restriction and/or Election Requirement.

U.S. Appl. No. 12/271,480, filed May 21, 2007, Sep. 2, 2010 Response to the Aug. 6, 2010 Restriction and/or Election Requirement.

(56) References Cited

OTHER PUBLICATIONS

U.S. Appl. No. 12/271,480, filed May 21, 2007, Nov. 3, 2010 Non-Final Office Action.
U.S. Appl. No. 12/271,480, filed May 21, 2007, Apr. 28, 2011 Response to the Nov. 3, 2010 Non-Final Office Action.
Wan et al., "Plasticizers and their effects on microencapsulation process by spray-drying in an aqueous system," J. Microencapsulation, vol. 9(1), pp. 53-62 (1992).
Watkins, Paul, "The Barrier Function of CYP3A4 and P-Glycoprotein in the Small Bowel," Advanced Drug Delivery Reviews, vol. 27, pp. 161-170 (1997).
Benzonana, et al., "Etude Cinetique de L'Action de la Lipase Pancreatique Sur Des Triglycerides en Emulsion Essai D'Une Enzymologie en Milieu Heterogene," Biochimica Et Biophysica ACTA, 105:121-136 (1965) (English Abstract).
Bezzine, et al., "Human Pancreatic Lipase: Colipase Dependence and Interfacial Binding of Lid Domain Mutants," Biochemistry 23:5499-5510 (1999).
Borgstrom, et al., "Pancreatic Juice Co-Lipase: Physiological Importance," Biochimica Et Biophysica ACTA, 242:509-513 (1971).
Borgstrom, et al., "Pancreatic Lipase and Colipase: Interaction and Effect of Bile Salts and Other Detergents," Eur. J. Biochem, 37:60-68 (1973).
Borgstrom, "Binding of Pancreatic Colipase to Interfaces; Effects of Detergents," FEBS Letters, 71(2):201-204 (1976).
Borgstrom, "On the Interactions Between Pancreatic Lipase and Colipase and the Substrate and the Importance of Bile Salts," Journal of Lipid Research, 16:411-417 (1975).
EP 1931317, Aptalis Pharma S.r.L, Submission of Opponent 02 in Preparation of Oral Proceedings, Aug. 3, 2011.
EP 1931317, Nordmark Arzneimittel GmbH & Co. KG, Submission of Opponent 01 in Preparation of Oral Proceedings, Jul. 20, 2011 (with Translation).
Gargouri, et al., "Studies on the Detergent Inhibition of Pancreatic Lipase Activity," Journal of Lipid Research, 24:1336-1342 (1983).
Saunders, et al., "Lecithin Inhibits Fatty Acid and Bile Salt Absorption from Rat Small Intestine In Vivo," Lipids, 11 (12):830-832 (1976).
Ammon, et al., "Effect of Lecithin on Jejunal Absorption of Micellar Lipids in Man and on Their Monomer Activity in vitro," Lipds, 14(4):395-400 (1978).
Jones, et al., "Effects of Exogenous Emulsifiers and Fat Sources on Nutrient Digestibility, Serum Lipids, and Growth Performance in Weanling Pigs," J. Anim Sci., 70:3473-3482 (1992).
Kammlott, et al., "Experiments to Optimize Enzyme Substitution Therapy in Pancreatic Duct-Ligated Pigs," Journal of Animal Physiology and Animal Nutrition, 89:105-108 (2005).
Lukovac, et al., "Gelucire 44/14 Improves Fat Absorption in Rats with Impaired Lipolysis," Biochimica et Biophysica Acta, 1801:665-673 (2010).
O'Doherty, et al., "Role of Luminal Lecithin in Intestinal Fat Absorption," Lipids, 8(5):249-255 (1972).
Overland, et al., "Lecithin in Swine Diets: I. Weanling Pigs," J. Anim Sci, 71:1187-1193 (1993).
Overland, et al., "Effect of Lecithin on the Apparent Ileal and Overall Digestibility of Crude Fat and Fatty Acids in Pigs," J. Anim Sci, 72:2022-2028 (1994).
Tabeling, et al., "Studies on Nutrient Digestibilities (Pre-Caecal and Total) in Pancreatic duct-Ligated Pigs and the Effects of Enzyme Substitution," J. Anim. Physiol. a. Anim. Nutr., 82:251-263 (1999).
Axcan Pharma, Inc., Viokase Prescribing Information, Mar. 2000, 3 pages.
Bieger, W. et al., "Two-dimensional isoelectric focusing/sodium dodecyl sulfate gel electrophoresis of protein mixtures containing active or potentially active proteases analysis of human exocrine pancreatic proteins," Anal. Biochem. (1980) 109:222-230.
Braeuniger, S. et al., "Further studies on thermal resistance of bovine parvovirus against moist and dry heat," Int. J. Hyg. Environ. Health (2000) 203:71-75.

Challapalli, K.K. et al., "High reproducibility of large-get two-dimensional electrophoresis," Electrophoresis (2004) 25:3040-3047.
Chueshov et al., Industrial Technology of Drugs and medicine, vol. 2, NFAU Publishing House, pp. 359-363 (2002) with translation.
Cunningham, N. et al., "Replication of avian infectious bronchitis virus in African green monkey kidney cell line VERO," J. Gen. Virol. (1972) 16:423-427.
DeRobertis, Cell & Mol. Biol. (1980) 7th Ed., 132-133.
Directive 2003/36/EC of the European Parliament and of the Council of May 26, 2003, Official Journal of the European Union, p. L 156/26-30.
Definition of "picornaviridae," http://medical-dictionary.thefreedictionary.com/Picornaviridae, downloaded Jul. 26, 2011.
Dony, J. et al., "Etide electrophoretique et immunoelectrophoretique de preparations enzymatiques injectables: preparation d'origine pancreatique et preparations d'origine testiculaire," progress in Immunological Standardization (1970) 4:395-405, with English translation.
Fallis, LS. et al., "Observations on some metabolic changes after total pancreatoduodenectomy," Annals of Surgery (1948) 639-667.
"Gastric juice" (http://www.thefreedictionary.com/gastric+juice) accessed Aug. 2, 2013.
Goerg, A et al., "The current state of two-dimensional electrophoresis with immobilized gH gradients," Electrophoresis (2000) 21:1037-1053.
Goldman, D. et al., "Human lymphocyte polymorphisms detected by quantitative two-dimensional electrophoresis," Am. J. Hum. Genet. (1983) 35:827-837.
Goodman & Gilman's "The Pharmacological Basis of Therapeutics," 8th Edition, Pergamon Press (1990) 1471-1477.
Jenkins, L.W. et al., "Conventional and functional proteomics using large formal two-dimensional gel electrophoresis 24 hours after controlled cortical impact in postnatal day 17 rats," J. Neurotrauma (2002) 19(6):715-740.
Kirk-Othmer, Encyclopedia of Chemical Technology, 3rd Edition, 23:724-25 (1984).
Klotz, H.P., "Lyophilized pancreatic extract, an aid in the treatment of mild diabetes," La Nouvelle Presse Medicals (1975) 4(32):2333, abstract.
Korneeva, O.S. et al., "Identification of catalytically active groups of wheat (Triticum aestivum) germ lipase," Appl. Biochem. & Microbiol. (2008) 44(4):349-355.
Korzhavykh et al., "Tablets and their various forms," Russian Pharmacies (2010) 19:1-5 with translation.
Marumerizer QJ-1000T Spheronizer (http://www.lcicorp.com/industrial_granulation/detail/category/marumerizer_qj1000 (accessed Jul. 26, 2013).
May et al., J. Biol. Standardization (1982) 10:249-259.
Meyer, Boyd Anal. Chem. (1959) 31:215-219.
Murlin et al., "The influence of alkili upon the glycos uria, hyperglycemia and carbon dioxide combining power in human diabetes," Proceedings of the Society for Experimental Biol. Med. (1917) 14:8-9.
Nishihara, J.C. et al., "Quantitative evaluation of proteins in one- and two-dimensional polyacrylamide gels using a fluorescent stain," Electrophoresis (2002) 23:2203-2215.
Padfield, P.J. et al., "The use of two-dimensional gel electrophoresis and high-performance liquid chromatography for the analysis of pancreatic juice," The Pancreas: Biology, Pathbiology, and Disease, Second Edition, Chapter 14 (1993) 265-273.
Pariza, M.W. et al., "Evaluating the safety of microbial enzyme preparations used in food processing: update for a new century," Regul. Toxicol. Pharmacol. (2001) 33(2):173-186.
Porter, S.C., "Coating of pharmaceutical dosage forms," Chapter 46, Remington: The Science and Practice of Pharmacy, Lippincott, Williams & Wilkins, Philadelphia (2005) 21st Edition, Chapter 46:929-938.
Register of Pharmaceuticals in Russia, RP-Pharmacist, Annual Collection, Issue 5, p. 772 (2003) with translation.
Ridder, G. et al., "Quantitative analysis of pattern recognition of two-dimensaional electrophoresis gels," Clin. Chem. (1984) 30(12):1919-1924.

(56) References Cited

OTHER PUBLICATIONS

Scharpe, S. et al., "Isoelectric characterization of porcine pancreative alpha amylases," Journal De Pharmacie De Belgique (1973) 28(6):705-708.
Scheele, G.A., "Two-dimensional gel analysis of soluble proteins," J. Biol. Chem. (1975) 250(14):5375-5385.
Shimura, K. et al., "Affinophoresis in two-dimensional agarose gel electrophoresis specific separation of biomolecules by a moving affinity ligand," Anal. Biochem. (1987) 161(1):200-206.
Smolka, M. et al., "Quantitative protein profiling using two-dimensional gel electrophoresis, isotope-coded affinity tag labeling, and mass spectrometry," Mol. Cell Proteomics (2002) 1.1:19-29.
Thoma et al., "Influence of aqueous coatings on the stability and enteric coated pellets and tablers," Eur. J. Pharmaceu. Biopharma. (1999) 47:39-50.
Van Den Bergh, G. et al., "Fluorescent two-dimensional difference gel electrophoresis and mass spectrometry identify age-related protein expression differences for the primary visual cortex of kitten and adult cat," J. Neurochem. (2003) 85:193-205.
Veronese et al., "Photo inactivation of enzymes by linear and angular furocoumarins," Photochem & Photobiol. (1982) 36(1):25-30.
Voss, T. et al., "Observations on the reproducibility and matching efficiency of two-dimensional electrophoresis gels: consequences for comprehensive data analysis," Electrophoresis (2000) 21:3345-3350.
Notices of Opposition filed by Nordmark Arzneimittel GmbH & Co. KG and Eurand S.p.A., EP 1931317; Reply of the Patent Proprietor to the Notice of Opposition (Jun. 7, 2010).
European Patent Office Search Report and Opinion for Application No. 07120740.1 dated Mar. 1, 2008.
European Search Report for Application No. 97114330 dated Jun. 5, 2002.
European Patent Office Search Report for Application No. 10178590 dated Dec. 9, 2010.
International Preliminary Report on Patentability for Application No. PCT/EP2004/008332 dated Jan. 30, 2006.
International Search Report and Written Opinion for Application No. PCT/EP2005/051295 dated Jun. 24, 2005.
International Search Report for Application No. PCT/EP2004/008332 dated Nov. 24, 2004.
International Search Report for Application No. PCT/EP2007/054880 dated Sep. 18, 2007.
Written Opinion for Application No. PCT/EP2006/065311 dated Feb. 2, 2007.
Written Opinion for Application No. PCT/EP2007/054880 dated Sep. 18, 2007.
United States Patent Office Action for U.S. Appl. No. 11/464,754 dated Sep. 2, 2009 (18 pages).
United States Patent Office Action for U.S. Appl. No. 11/464,754 dated Jun. 1, 2010 (16 pages).
United States Patent Office Action for U.S. Appl. No. 11/464,754 dated Aug. 16, 2013 (26 pages).
United States Patent Office Action for U.S. Appl. No. 11/085,073 dated Oct. 23, 2006 (12 pages).
United States Patent Office Action for U.S. Appl. No. 11/085,073 dated Jul. 13, 2007 (13 pages).
United States Patent Office Action for U.S. Appl. No. 11/085,073 dated Apr. 7, 2008 (17 pages).
United States Patent Office Action for U.S. Appl. No. 11/085,073 dated Feb. 26, 2010 (19 pages).
United States Patent Office Action for U.S. Appl. No. 11/460,330 dated Nov. 12, 2010 (13 pages).
United States Patent Office Action for U.S. Appl. No. 11/460,330 dated Aug. 4, 2011 (21 pages).
United States Patent Office Action for U.S. Appl. No. 11/460,330 dated Apr. 9, 2012 (21 pages).
United States Patent Office Action for U.S. Appl. No. 11/464,704 dated Aug. 21, 2009.
United States Patent Office Action for U.S. Appl. No. 11/464,704 dated May 26, 2010.
United States Patent Office Action for U.S. Appl. No. 11/464,704 dated Aug. 2, 2013 (21 pages).
United States Patent Office Action for U.S. Appl. No. 12/271,480 dated Jul. 14, 2011 (12 pages).
United States Patent Office Action for U.S. Appl. No. 12/271,480 dated May 24, 2013 (14 pages).
United States Patent Office Action for U.S. Appl. No. 12/271,480 dated Sep. 19, 2013 (13 pages).
Copending U.S. Appl. No. 14/074,255, filed Nov. 7, 2013.
United States Patent Office Action for U.S. Appl. No. 11/460,330 dated Oct. 18, 2013 (22 pages).
U.S. Appl. No. 60/708,526 by George Shlieout et al., filed Aug. 15, 2005.
Biswal, S. et al, "Production variables affecting characteristics of pellets in melt pellitization with wax combination in a laboratory scale spheronizer," Acta Pharm. (2009) 59:199-210.
Loa, C.C. et al., "Purification of turkey coronavirus by stephacryl size-exclusion chromatography," J. Virol. Meth. (2002) 104:187-194.
Mesiha, M.S. et al., "A screening study of lubricants in wet powder masses suitable for extrusion-spheronization," Drug Dev. & Ind. Pharm. (1993) 19(8):943-959.
PEG 4000, EM Grade, Technical Data Sheet 279, Polysciences, Inc. (1999) 2 pages.
ShinEtsu Chemical Company, USP Hypromellose Phthalate Enteric Coating Material (Sep. 2002) 10 pages.
Tabasi, S.H. et al., "Quality by design, Part I: Application of NIR spectroscopy to monitor tablet manufacturing process," J. Pharm. Sci. (2008) 97:4040-4051.
Tabasi, S.H. et al., "Quality by design, Part II: Application of NIR spectroscopy to monitor the coating process for a pharmaceutical sustained release product," J. Pharm. Sci. (2008) 97:4052-4066.
Ueba, O., "Respiratory synctial virus. I. Concentration and purification of the infectious virus," Acta Medica Okayama (1978) Article 2, 32(4):265-272.
U.S. Pharmacopeia 28, National Formulary 23, 23rd Edition, (2004) 10 pages.
Written Submission by Opponent in the Opposition filed by Aptalis Pharma S.r.L. against European Patent No. 1931316 dated May 4, 2012.
Aptalis Farma S.r.L., Certificate of Inscription in the Regular Identification Data of the Company (Jul. 15, 2011) 4 pages.
Decision to Revoke the European Patent No. EP1931317 in the Opposition filed by Nordmark against European Patent No. 1931317 dated Nov. 17, 2011.
Grounds of Appeal in the Opposition filed by Aptalis Pharma S.r.L. against European Patent No. 1931316 dated Jan. 2, 2013.
Grounds of Appeal in the Opposition filed by Nordmark against European Patent No. 1931317 dated Mar. 15, 2012.
Reply from Opponent in the Opposition filed by Nordmark against European Patent No. 1931317 dated Jul. 20, 2012.
Reply of Proprietor in the Opposition filed by Aptalis Pharma S.r.L. against European Patent No. 1931316 dated Jun. 7, 2011.
Reply to Appeal in the Opposition filed by Nordmark Against European Patent No. 1931317 dated Sep. 28, 2012.
Reply to Appeal in the Opposition filed by Aptalis Pharma S.r.L. against European Patent No. 1931316 dated May 13, 2013.
Reply to Summons to Attend Oral Proceedings: filing of new main claim request in the Opposition filed by Aptalis Pharma S.r.L. against European Patent No. 1931316 dated Feb. 23, 2012.
Reply to Summons to Attend Oral Proceedings: New Written Submissions and Claim Amendments in the Opposition filed by Nordmark against European Patent No. 1931317 dated Aug. 4, 2011.
Results and Minutes of Oral Proceedings in the Opposition filed by Aptalis Pharma S.r.L. against European Patent No. 1931316 dated Sep. 5, 2012.
Results and Minutes of Oral Proceedings in the Opposition filed by Nordmark against European Patent No. 1931317 dated Oct. 6, 2011.

(56) References Cited

OTHER PUBLICATIONS

Summons to Oral Proceedings in the Opposition filed by Aptalis Pharma S.r.L. against European Patent No. 1931316 dated Dec. 22, 2011.
Summons to Oral Proceedings in the Opposition filed by Nordmark Arzneimittel GmbH against European Patent No. 1931317 dated Mar. 29, 2011.
Technical Reports on Comparative Exp.x, examples 1/7 thru 7/7 (2009), including B810586 "PEG4000 iprop high"; B810587 "PEG2000"; B810588 "PEG8000"; B810589 "HPMC iprop equ"; B810590 "PVP iprop equ"; B810591 "HPMC iprop high"; and B810592 "PVP iprop low".
Written Submission in the Opposition filed by Nordmark against European Patent No. 1931317 dated Aug. 25, 2011.
Written Submission by Aptalis Pharma S.r.L. In the Opposition filed by Aptalis Pharma S.r.L. against European Patent No. 1931316 dated Mar. 12, 2012.
United States Patent Office Action for U.S. Appl. No. 12/271,480 dated Jan. 6, 2015 (15 pages).
United States Patent Office Action for U.S. Appl. No. 11/464,754 dated Apr. 23, 2014 (31 pages).
United States Patent Office Notice of Allowance for U.S. Appl. No. 11,085,073 dated Apr. 1, 2014 (17 pages).
United States Patent Office Action for U.S. Appl. No. 11/460,330 dated Jun. 2, 2014 (23 pages).
United States Patent Office Action for U.S. Appl. No. 11/464,704 dated Apr. 25, 2014 (25 pages).
Tabasi, S.H. et al., "Quality by design, Part III: study of curing process of sustained release coated products using NIR spectroscopy," J. Pharm. Sci. (2008) 97:4067-4086.
United States Patent Office Action for U.S. Appl. No. 11/460,330 dated Jun. 5, 2015 (38 pages).
United States Patent Office Notice of Allowance for U.S. Appl. No. 12/271,480 dated Jul. 20, 2015 (13 pages).
United States Patent Office Notice of Allowance for U.S. Appl. No. 11/464,754 dated Jul. 27, 2015 (17 pages).
United States Patent Office Action for U.S. Appl. No. 11/464,704 dated Jul. 28, 2015 (26 pages).
United States Patent Office Action for U.S. Appl. No. 11/460,330 dated Sep. 24, 2015 (39 pages).
Die Tablette, Handbuch der Entwicklung, Herstellung and Qualitatssicherung, Editiv cantor Verlag Aulendorf (2002) Seiten 85-89, 91-106, 583, 584, W.A. Ritschel eds. with English translation.
Pharmazeutische Technologie, Georg Thieme Verlag Stuttgart (1978/1991) 2:178-179, with English translation.
Reply from Opponent in the Opposition filed by Nordmark against European Patent No. 1931317 dated Jul. 20, 2012, with English translation.
Rompp Chemie Lexikon, Jurgen Falbe et al. editors, (1992) Georg Thieme Verlag, 9:3532 "Polyethylenglykole," with English translation.
Written Submission in the Opposition filed by Nordmark against European Patent No. 1931317 dated Aug. 25, 2011, with English translation.
Buhler, V., Polyvinylpyrrolidone Excipients for Pharmaceuticals, Povidone, Crospovidone and Copovidone (2005) 1-254, Springer-Verlag.
Luwa, http://www.icicorp.com/industrial_granulation, accessed Dec. 16, 2015.
Rudric, E.M. et al., "Oral solid dosage forms," Remington: The Science and Practice of Pharmacy, 21st Edition (2005) Chapter 45, 889-928.
United States Patent Office Action for U.S. Appl. No. 11/464,704 dated Dec. 24, 2015 (20 pages).
USPTO Office Action for U.S. Appl. No. 12/271,480, dated Mar. 24, 2016.
Mbiguino, A. et al., "Purification of human respiratory syncytial virus: superiority of sucrose gradient over percoll, renografin, and metrizamide gradients." J Virol. Methods, 1991, vol. 31(2-3), pp. 161-170.

\* cited by examiner

PROCESS FOR SEPARATING AND DETERMINING THE VIRAL LOAD IN A PANCREATIN SAMPLE

CROSS-REFERENCE TO RELATED APPLICATIONS

This application claims the benefit of U.S. Provisional Application No. 60/747,891 filed May 22, 2006, which is hereby incorporated by reference in its entirety to the extent permitted by law.

TECHNICAL FIELD

Processes for separating an infectious viral load from a pancreatin sample and for quantitatively determining the viral load in a pancreatin sample are described herein.

BACKGROUND

Pancreatin is a mixture of several physiologically-active constituents and is typically derived from mammalian pancreatic glands. The main constituents of pancreatin are digestive enzymes, in particular pancreatic lipase, amylases and proteases. Due to its important therapeutic properties and high level of safety, pancreatin has long been used as a pharmaceutical preparation in enzyme replacement therapy. Pancreatin has been used to treat pancreatic exocrine insufficiency which is often associated with cystic fibrosis, chronic pancreatitis, post-pancreatectomy, post-gastrointestinal bypass surgery (e.g. Billroth II gastroenterostomy) and ductal obstruction from neoplasm (e.g. of the pancreas or common bile duct). The therapeutic benefits of pancreatin are generally attributed to pancreatic lipase as well as the amylases and proteases. Pancreatin is typically derived from cattle ("bovine pancreatin") or pigs ("porcine pancreatin"), with porcine pancreatin being more significant in terms of quantity of pancreatin produced. Methods for the production of pancreatin for therapeutic purposes have been previously described, for example in U.S. Pat. No. 4,623,624.

Due to the nature of animal derived pancreatin, the starting materials are typically accompanied by unwanted biological components, such as bacterial or viral contaminants. However, during more than 100 years of commercialization of pharmaceutical products containing pancreatin, no case has been reported where patients have been affected by viral-contaminated pancreatin. Nevertheless, companies producing pharmaceutical products derived from biological tissues and/or body fluids are experiencing additional pressure from the regulatory bodies to increase the level of safety of their products by reducing all contaminants to the lowest level possible, independent of whether any concerned contaminant is considered a human pathogen or not. For the manufacture and use of pharmacological products containing pancreatin, it is therefore desirable to have reliable analytical methods for detecting and quantifying such biological contaminants.

To date, no reliable method has been developed for quantitatively detecting or separating viral contaminants in a pancreatin sample. This is likely due to the fact that the enzymatically active constituents of pancreatin are incompatible with the cell lines typically used for multiplying viruses, thus making it more difficult or even impossible to determine the virus titer in a pancreatin sample.

Accordingly, one object of the present disclosure is separating an infectious viral load from a pancreatin sample and for quantitatively determining the viral load in a pancreatin sample.

It has now been surprisingly found that the viral load of a pancreatin sample may be quantized when the viral load is first separated from the pancreatin sample using a multistage centrifugation process.

SUMMARY

Described herein is a process for separating the viral load in a pancreatin sample from other components of the sample using a multistage centrifugation process. An additional embodiment is the determination of the viral titer level in the pancreatin sample. Additional embodiments include methods for treating pancreatin exocrine insufficiency, pharmaceutical compositions comprising pancreatin and processes for the manufacture of pancreatin.

Other embodiments, objects, features and advantages will be set forth in the detailed description of the embodiments that follows, and in part will be apparent from the description, or may be learned by practice, of the claimed invention. These objects and advantages will be realized and attained by the processes and compositions particularly pointed out in the written description and claims hereof. The foregoing Summary has been made with the understanding that it is to be considered as a brief and general synopsis of some of the embodiments disclosed herein, is provided solely for the benefit and convenience of the reader, and is not intended to limit in any manner the scope, or range of equivalents, to which the appended claims are lawfully entitled.

DESCRIPTION

While the present invention is capable of being embodied in various forms, the description below of select embodiments is made with the understanding that the present disclosure is to be considered as an exemplification of the claimed subject matter, and is not intended to limit the appended claims to the specific embodiments illustrated. The headings used throughout this disclosure are provided for convenience only and are not to be construed to limit the claims in any way. The various embodiments disclosed herein may be combined with other embodiments for the creation and description of yet additional embodiments.

The process described herein is suitable for all types of animal-derived pancreatin, such as those of porcine or bovine origin. Additionally, the processes described herein are suitable for separating a viral load from a pancreatin sample to allow for subsequent titer level determination. Viruses which can be quantized according to the methods described herein include bovine rotavirus A, encephalomyocarditis virus (EMCV), porcine circovirus (PCV), porcine parvovirus (PPV), porcine rotavirus A, porcine teschovirus and swine vesicular disease virus (SVDV). Due to their similar properties, the human coxsackievirus B 5/1 may be used as a substitute for SVDV, bovine rotavirus A (for example strain B 223) may be used as a substitute for porcine rotavirus A in assessing the processes described herein.

The method of separating the viral load from a pancreatin sample comprises preparing a liquid pancreatin test sample suitable for centrifugation from the pancreatin sample. Preferably, the liquid pancreatin test sample is prepared without altering the viral load of the pancreatin sample to be evaluated. A liquid pancreatin test sample may be prepared as a suspension by combining the pancreatin sample with a cell culture medium suitable for the cell line used to culture the virus species to be investigated along with one or more antibiotic(s).

The liquid pancreatin test sample can optionally include an antibiotic. In general, any antibiotic is suitable for inclusion in the liquid pancreatin test sample, such as broad-spectrum antibiotics or mixtures of broad-spectrum antibiotics. One or more antibiotics may be selected from the group comprising β-lactam antibiotics such as penicillins, cephalosporins (including oxacephemes and carbacephemes), carbapenemes and monobactames; streptomycin (including streptomycin sulfate); neomycins (including neomycin A, neomycin B and paromomycin); kanamycins (including kanamycin, gentamicin, amicacin and tobramycin); spectinomycin; tetracyclins (including tetracyclin, oxytetracyclin, doxycyclin and minocyclin); macrolide antibiotics (including erythromycin, clarithromycin, roxithromycin, azithromycin, josamycin and spiramycin); gyrase inhibitors (including nalidixin acid, cinoxacin, pipemidic acid, norfloxacin, pefloxacin, ciprofloxacin, ofloxacin and fleroxacin; folic acid antagonists (including sulfonamide antibiotics, diamino benzylpyrimidines and their combinations); chloramphenicol; lincosamides; glycopeptide antibiotics (including vancomycin and teicoplanin); fosfomycin; polypeptide antibiotics (including polymixin B, colistin, bacitracin and tyrothicin) and mupirocin. Other suitable antibiotics can be found in *Remington's: The Science and Practice of Pharmacy,* 21$^{th}$ ed., *The Merck Index,* 14$^{th}$ ed. and *Goodman and Gilman's, The Pharmacological Basis of Therapeutics,* 11$^{th}$ ed. each of which are hereby incorporated by reference in their entirety. The liquid pancreatin test sample may also include one or more solvents which are compatible with pancreatin and any antibiotic(s) which may be used.

The pancreatin test sample suspension can be prepared by cooling it to a temperature between about 0° C. and about 15° C., for example about 0° C., about 1° C., about 2° C., about 3° C., about 4° C., about 5° C., about 6° C., about 7° C., about 8° C., about 9° C., about 10° C., about 11° C., about 12° C., about 13° C., about 14° C., or about 15° C., and preferably between about 4° C. and about 15° C.

To prepare a liquid pancreatin test sample, the components are stirred in an ice bath between about 30 minutes and about 120 minutes, for example about 30 minutes, about 35 minutes, about 40 minutes, about 45 minutes, about 50 minutes, about 55 minutes, about 60 minutes, about 65 minutes, about 70 minutes, about 75 minutes, about 80 minutes, about 85 minutes, about 90 minutes, about 95 minutes, about 100 minutes, about 105 minutes, about 110 minutes, about 115 minutes and about 120 minutes. Cooling of the pancreatin test sample is to avoid, or at least minimize, unwanted deactivation of the virus to be separated and quantized by the enzymatically active constituents of the pancreatin sample. A further embodiment includes a pancreatin test sample in the form of a suspension which optionally includes an antibiotic as previously described.

The cell culture media to be used as a component of the test sample suspension is determined by the viral species to be separated or quantized. Suitable cell cultures are those in which the viral species to be investigated initiates, if possible, a cytopathic effect (CPE) and are used for culturing and detecting a specific virus species. CPE is a modification of virus-infected cells which is recognizable by light microscopy. If a virus species multiplies in the culture cell without CPE, such multiplication may typically be identified by indirect detection methods known to a person of ordinary skill in the art.

If bovine rotavirus A is to be separated or quantized, fetal monkey kidney cells (MA-104 cells) may be used for culturing of the virus. In this case, Dulbecco's Modified Eagle Medium (Dulbecco medium) is a suitable cell culture medium. If EMCV is to be separated or quantized, porcine kidney cells (PK-15 cells) or embryonal porcine kidney cells (SPEV cells) may be used for culturing the virus. In the case of PK-15 cells, Minimal Essential Medium (MEM) is a suitable cell culture medium. In the case of SPEV cells, Dulbecco medium is suitable as the cell culture medium. If PCV is to be separated or quantized, PK-15 cells may be used for culturing the virus. If PPV is to be separated or quantized, porcine kidney cells (SK-6 cells) may be used for culturing the virus with Dulbecco medium being a suitable cell culture medium. If porcine rotavirus A is to be separated or quantized, MA-104 cells may be used for culturing the virus. If porcine teschovirus is to be separated or quantized, PK-15 cells may be used for culturing the virus. If SVDV is to be separated or quantized, SPEV cells may be used for culturing the virus. A person of ordinary skill in the art would recognize that other cell lines and/or cell culture media, other than those specifically identified, are suitable for culturing the particular viral species to be separated or quantized. Viral species and corresponding cell lines suitable for use may be obtained from sources such as the "American Type Culture Collection", Manassas, USA (ATCC), the "Deutsche Sammlung von Mikroorganismen und Zellkulturen GmbH", Braunschweig, Germany (DSMZ), the "Friedrich-Löffler-Institut", Federal Research Institute for Animal Health, Insel Riems, Germany (FLI) or the "Veterinary Service Division" of the "Department of Agriculture and Rural Development", Belfast, United Kingdom (DARD).

The pancreatin test sample prepared as previously described may either be used in its entirety or a defined portion thereof may be used. Preferably, the pancreatin test sample is used in its entirety.

The process for separating a viral load from a pancreatin sample further comprises subjecting at least part of the liquid pancreatin test sample to low-speed centrifugation. Low-speed centrifugation includes those conditions under which viruses with sedimentation constants of greater than about 120 S, in particular greater than about 120 S, greater than about 150 S, greater than about 200 S, greater than about 250 S, greater than about 300 S, greater than about 350 S, greater than about 400 S, greater than about 450 S, greater than about 450 S, greater than about 500 S, greater than about 1000 S, greater than about 1500 S, greater than about 2000 S, greater than about 2500 S, greater than about 3000 S, greater than about 3500 S, greater than about 4000 S, greater than about 4500 S and greater than about 5,000 S, do not form a pellet. Typically, viruses with sedimentation constants of greater than about 120 S, in particular viruses with sedimentation constants of greater than about 120 S to about 5,000 S, do not form pellets when the low-speed centrifugations are carried out with a relative centrifugal force of less than about 10,000×g. The relative centrifugal force of the low-speed centrifugation is less than about 10,000×g such as about 9500, about 9000, about 8500, about 8000, about 7500, about 7000, about 6500, about 6000, about 5500, about 5000, about 4500, about 4000, about 3500, about 3000, about 2500, about 2000, about 1500, about 1000 and about 500, preferably between about 1,500×g and about 5,000×g, more preferably between about 2,000×g and about 3,500×g (such as about 2100, about 2200, about 2300, about 2400, about 2500, about 2600, about 2700, about 2800, about 2900, about 3000, about 3100, about 3200, about 3300 and about 3400) and most preferably about 2,700×g.

The duration of low-speed centrifugation is about 5 minutes, usually between about 5 and about 60 minutes, such as about 5 minutes, about 10 minutes, about 15 minutes, about 20 minutes, about 25 minutes, about 30 minutes, about 35 minutes, about 40 minutes, about 45 minutes, about 50 minutes, about 55 minutes, about or about 60 minutes. In one embodiment, low-speed centrifugation is carried out in a refrigerated centrifuge with cooling such that the temperature of the liquid pancreatin test sample is between about 0° C. and about 15° C., such as about 0° C., about 1° C., about 2° C., about 3° C., about 4° C., about 5° C., about 6° C., about 7° C., about 8° C., about 9° C., about 10° C., about 11° C., about 12° C., about 13° C., about 14° C. and about 15° C.

The purpose of low-speed centrifugation is primarily to remove those constituents (e.g., insoluble particles) which are disruptive to, or incompatible with, the separation or quantitative determination of the viral load in a pancreatin sample and to obtain a pancreatin test sample supernatant which is suitable for further processing. The solid deposits optionally obtained in low-speed centrifugation steps are thus generally discarded while the supernatant is subject to further processing. Low-speed centrifugation with subsequent discarding of the solid deposits is repeated until solid deposits no longer form. Typically, low-speed centrifugation only needs to be carried out once with subsequent discarding of the solid deposits; however, this process may be repeated to obtain the desired level of solids removal. The pancreatin test sample supernatant and solid deposits or sediment resulting from the low-speed centrifugation each form additional embodiments of the invention described herein.

In one embodiment, the deposit obtained from the low-speed centrifugation is washed one or more times with a suitable washing fluid before being discarded. A suitable washing fluid is, for example, the pancreatin test sample supernatant resulting from low-speed centrifugation. If a washing fluid other than the pancreatin test sample supernatant is used, the washing fluid is combined with the pancreatin test sample supernatant after washing. It is particularly advantageous to wash the deposit in the above-stated manner prior to further processing if the viral load of the pancreatin sample comprises EMCV.

The process of separating a viral load from pancreatin further comprises subjecting at least part of the pancreatin test sample supernatant to ultracentrifugation in a discontinuous gradient medium. The conditions of ultracentrifugation (duration and magnitude of the relative centrifugal force) are selected such that the transportation of the viral load from the pancreatin test sample supernatant to a target fraction of the discontinuous gradient is substantially complete.

A discontinuous two-phase sucrose gradient is used as the discontinuous gradient medium. The discontinuous gradient medium preferably comprises a gradient prepared from a buffered sucrose solution which is about 50% (wt./vol.) and a buffered sucrose solution which is about 20% (wt./vol.). Neutral buffers (i.e. those which buffer around pH 7) may be used as the buffer for the sucrose solutions. A PBS buffer (phosphate-buffered saline buffer, pH 7.2) is preferred. Sterile gradient media can also be used. This two-phase discontinuous sucrose gradient provides suitable sedimentation and thus separation conditions for the viruses typically associated with animal-derived pancreatin. Discontinuous sucrose gradients, in particular the gradient previous described, exhibit suitable osmotic conditions which will not deactivate the viral load. By using ultracentrifugation, the transfer of the viral load from the pancreatin test sample supernatant into the discontinuous gradient medium is substantially complete. Substantially complete as used in connection with the ultracentrifugation step means that a viral load previously added to a test sample is so completely recovered in the discontinuous gradient medium that the difference between viral titer level of the added viral load and in that recovered after ultracentrifugation is less than or equal to one half step of the base-ten logarithm of virus titer (0.5 log steps). Use of ultracentrifugation allows for the viral load to be transported into a target fraction which is sufficiently far from the pancreatin test sample which permits mechanical separation of the target fraction from the pancreatin test sample without any remixing or other disruption of the separated phases occurring.

Creation of the discontinuous two-phase gradient and subsequent ultracentrifugation is carried out by introducing a volume of the highest concentration gradient medium into an ultracentrifuge tube over which is layered a volume of the next lower concentration gradient media. This process is repeated as many times as desired to obtain a multi-phase gradient medium with the final (top) layer being a volume of liquid pancreatin test sample suitable for centrifugation from which the viral load is to be separated. In the case of a two-phase gradient medium, the volume of the next lower concentration gradient medium is then immediately overlayed with a volume of a liquid pancreatin test sample (pancreatin test sample volume) which is suitable for centrifugation. In the case of a two-phase gradient medium, this yields a sequence of layers in the ultracentrifuge tube from the top down of a first layer comprising the liquid pancreatin test sample (top), then the volume of the lowest concentration gradient medium (middle; for example a 20% (wt./vol.) buffered sucrose solution) and finally the volume of the highest concentration gradient medium (bottom, covering the base of the ultracentrifuge tube; for example a 50% (wt./vol.) buffered sucrose solution). When overlaying the individual volumes, care must be taken to ensure that no turbulence or intermixing occurs at the respective boundaries.

The target fraction of the multi-phase gradient is typically (i) a part of the lowest-concentration gradient medium sufficiently removed from the pancreatin test sample volume; and (ii) the complete volume of the next higher concentration gradient medium. In the case of a two-phase gradient medium the target fraction comprises a part of the lowest concentration gradient medium sufficiently far away and remote from the pancreatin test sample volume and the complete volume of the highest concentration gradient medium extending downward to the bottom of the ultracentrifuge tube.

When calculating the location of a target fraction which is sufficiently removed from the pancreatin test sample volume thereby allowing for subsequent separation, it should be borne in mind that the calculated values for the position of the particles (i.e. the position of the viral particles separated from the pancreatin sample) usually denote the vertices of a Gaussian distribution. As such, the particles will be distributed both above and below their calculated position. It is thus necessary when determining the desired distance of the target fraction from the pancreatin test sample volume to include an additional margin to account for the Gaussian distribution of the particle locations. The viral load is transported into a target fraction which is sufficiently distant from the pancreatin test sample volume for subsequent separation if particles with a sedimentation constant of greater than about 120 S, in particular greater than about 120 S to about 5,000 S, have migrated from the pancreatin test sample volume at least about 10 mm, at least about 15 mm, at least about 20 mm, at least about 25 mm or at least about 30 mm, into the lowest concentration gradient medium due to the ultracentrifugation. In the case of the two-phase gradient medium previously described, the lowest concentration gradient medium is the 20% (wt./vol.) buffered sucrose solution. In one embodiment, substantially all of the viral particles with a sedimentation constant of greater than about 120 S, in particular greater than about 120 S to about 5,000 S, have passed through the lowest concentration gradient medium and are located at the boundary with the next higher concentration gradient medium (i.e. on a "sucrose cushion"). A person of ordinary skill in the art is aware of suitable ways of calculating and implementing the necessary conditions for obtaining the desired results from the ultracentrifugation. Suitable ultracentrifugation conditions may be determined based upon the characteristics of the virus(es) to be separated from the pancreatin sample (e.g., density and sedimentation constant) by a person of ordinary skill in the art (see for example Lebowitz et al., "Modern analytical ultracentrifugation in protein science: A tutorial review"; Protein Science 11 (2002) 2067-2079).

Provided that ultracentrifugation is carried out under suitable conditions and volume ratios and in the discontinuous gradient medium, the viral load will be transported into a target fraction of the discontinuous gradient medium and will be available for further analysis. Suitable ultracentrifugation conditions include carrying out ultracentrifugation for a duration of between about 1 hour and about 8 hours, such as at least about 1 hour, at least about 2 hours, at least about 3 hours, at least about 4 hours, at least about 5 hours, at least about 6 hours, at least about 7 hours or at least about 8 hours. Preferred durations include at least about 2 hours, for example between about 2 hours and about 8 hours, in particular for a duration of between about 3 hours and about 6 hours.

A suitable relative centrifugal force for the ultracentrifugation is at least about 100,000×g, for example between about 200,000 and about 350,000×g, such as about 200,000, about 225,000, about 250,000, about 275,000, about 300,000, about 325,000 or about 350,000. In one embodiment, the ultracentrifugation is carried out for a duration between about 3 hours and about 6 hours with a relative centrifugal force of between about 200,000 and about 350,000×g with volume ratios suitable for carrying out ultracentrifugation and in a gradient prepared from a 50% (wt./vol.) buffered sucrose solution and a 20% (wt./vol.) buffered sucrose solution. In another embodiment, the ultracentrifugation is carried out for a duration between about 3.5 hours and about 4.5 hours with a relative centrifugal force of between about 250,000 and about 300,000×g with a suitable volume ratio for carrying out ultracentrifugation and in a gradient prepared from a 50% (wt./vol.) buffered sucrose solution and a 20% (wt./vol.) buffered sucrose solution.

Suitable volume ratios for carrying out ultracentrifugation can be obtained, for example, by using conventional ultracentrifuge tubes. Conventional ultracentrifuge tubes are, for example, those with a volume of between about 10 ml and about 15 ml, in particular between about 12 ml and about 13 ml, and have an internal radius of between about 6 mm and about 8 mm, in particular about 7 mm, and have a height of between about 80 mm and about 100 mm, in particular between about 85 and about 95 mm. If a conventional ultracentrifugation tube is used with a two-phase gradient medium, then the volume of the highest concentration gradient medium (for example a 50% (wt./vol.) buffered sucrose solution) may be, for example, about 0.5 ml, the volume of the next lower concentration gradient medium (for example a 20% (wt./vol.) buffered sucrose solution) may be, for example, about 4.5 ml and the pancreatin test sample volume may be, for example, about 5 ml.

In one embodiment, independent of the other conditions, the temperature during ultracentrifugation of the pancreatin test sample supernatant is between about 0° C. and about 15° C., for example about 0° C., about 1° C., about 2° C., about 3° C., about 4° C., about 5° C., about 6° C., about 7° C., about 8° C., about 9° C., about 10° C., about 11° C., about 12° C., about 13° C., about 14° C., or about 15° C. and preferably between about 4° C. and about 15° C.

Refrigerated centrifuges which are suitable for use in the processes described herein are known to a person of ordinary skill in the art. Commercially available ultracentrifuges are suitable for use and include refrigerated ultracentrifuges with a swinging-bucket rotor, for example, an ultracentrifuge from Sorvall® with a model TH-641 swinging-bucket rotor.

The foregoing description of the low-speed centrifugation and ultracentrifugation may be scaled up or down to any desired extent and the descriptions provided herein are simply meant to illustrate a few embodiments of the claimed subject matter.

The process for separating a viral load from pancreatin further comprises quantitatively separating the target fraction containing the viral load from the pancreatin test sample supernatant. Separation can be undertaken by placing a mark on the ultracentrifuge tube at the location of the previously determined boundary of the target fraction. The entire volume above this boundary is then separated from the remaining volume by, for example, aspiration. Aspiration may proceed with a peristaltic pump which has been previously sterilized. A suitable pumping rate is about 2 ml/minute. During aspiration, care should be taken to ensure that the peristaltic pump capillary is located at the upper border of the liquid. The target fraction remaining in the ultracentrifuge tube may then be removed with a conventional single channel pipette, preferably with a sterile tip. Any sediment remaining in the ultracentrifuge tube may be removed at the same time by being repeatedly drawn up in the single channel pipette and resuspended.

The target fraction containing the viral load separated from the pancreatin test sample supernatant forms an additional embodiment of the invention described herein.

The process described herein optionally comprises an additional step of quantitatively determining the viral load of the pancreatin sample. In this optional step, the viral load of the pancreatin sample is quantized by determining the virus infection titer in the target fraction containing the viral load. This quantitative determination may proceed in accordance with methods known to those of ordinary skill in the art, for example, in accordance with the principle of virus infection titer determination (VITD).

The target fraction may, for example, be diluted in a suitable ratio with a compatible cell culture medium in order to obtain a suitable test sample for analysis. Compatible cell culture media are those previously identified in connection with each particular virus under investigation. A further embodiment includes ruling out false positives for viral infections by filtering the diluted or undiluted target fraction through a microfilter before the quantitative determination of the viral load is carried out.

A suitable dilution may, for example, be achieved by diluting the target fraction with the cell culture medium to the original volume of the pancreatin test sample supernatant. Then a series of dilutions of the virus determination test samples may be produced, for example, in dilution steps of 1:2, 1:5 or 1:10 or also in combinations of these dilution steps, in order to carry out a quantitative VITD. Then a cell suspension may be inoculated with the virus determination test samples of different concentrations from the dilution series, whereupon a cell layer is allowed to form on the differing concentrations of the virus determination test samples. To rule out false positives for virus infection which may be caused by the presence of microbials such as inert bacteria or mycoplasms, the virus determination test samples are filtered before inoculating them onto detector cells. A virus determination test sample or a diluted virus determination test sample may be filtered through a microfilter having a pore size between about 0.1 and about 10 µm, preferably a microfilter having a pore size of 1 µm. The filtrate may then be used as a test sample for further investigations. The inoculated test samples are then evaluated for their degree of infection depending upon the manner in which their infection is indicated. When CPE is used as an indicator of infection of a cell layer, it is read after between about 4 days and about 7 days. Titration (end-point dilution) of the virus determination test samples permits a quantitative determination of the viral load. Titration conventionally proceeds by dilution by a factor of 10, i.e. based on the base-ten logarithm. In practice, the 50% infection dose ($ID_{50}$) is usually calculated. In the case of parallel multiple batches, the identified $ID_{50}$ value then corresponds to that of the highest (reciprocal) dilution of the virus determination test sample at which a CPE is detectable in exactly half the batches. Optionally, the results may also be computationally corrected or interpolated. The most commonly used methods for virus titer calculation are those according to Spearman and Kärber (see C. Spearman, Br. J. Psychol. 2 (1908) 227-242 and G. Kärber, Arch. Exp. Path. Pharmak. 162 (1931) 480-483; also Bundesanzeiger [Federal gazette] no. 84, May 4 1994) or according to Reed and Muench (see Reed, L. J., Muench, H. Am. J. Hyg. 27 (1938) 493-497).

Other indicators of an infection of the cell layer may also be used, such as virus antigen induction or plaque induction. The person of ordinary skill in the art is familiar with these methods as well as others and the details of their application to the subject matter described herein. Additional information can be found, for example, in virology textbooks such as "Medizinische Virologie" by H. W. Doerr and W. H. Gerlich, Georg Thieme Verlag Stuttgart, New York, 1st edition 2002 or in each case the most recent edition thereof.

EXAMPLES

All tasks stated in the following Examples were carried out under sterile conditions on a sterile workbench. The following materials inter alia were used:
1. Antibiotic solution, 1.0 g of streptomycin sulfate and 1.2 g of penicillin are dissolved in 20 ml of twice-distilled water and filtered through a 0.2 µm filter. The filtrates are then divided into 1 ml aliquots and optionally stored at −20° C. until use;
2. Dulbecco medium, cell culture medium for SK 6 cells, SPEV cells and MA 104 cells;
3. Single channel pipette, with sterile tips;
4. FCS, fetal calf serum from Bio Whittaker (serum);
5. Tissue culture flasks, sterile, area of flask base in each case 25, 75 or 175 $cm^2$;
6. MEM, cell culture medium for PK-15 cells with 1.5 g/l sodium bicarbonate and 1 mM pyruvate;
7. Microtiter plates, sterile with 96 wells and lid;
8. PAN suspension,10% pancreatin suspension; 1.0 g of porcine pancreatin (unless otherwise stated) weighed out under sterile conditions into a beaker, combined with 1 ml of antibiotic solution and (unless otherwise stated) 8.0 ml of the particular corresponding cell culture medium and (unless otherwise stated) suspended within 60 minutes in an ice bath with stirring;
9. Pardee buffer, Pardee's carbon dioxide buffer;
10. PBS, sterile "phosphate buffered saline" solution (pH 7.2);
11. Pipettes, sterile;
12. Pipette tips, sterile in sterile trays;
13. Plastics pouches, $CO_2$-impermeable with closure ("Anaerocult®", from Merck);
14. Polyclonal anti-PPV antibody, fluorescein isothiocyanate (FITC) conjugate, from NatuTec GmbH;
15. Tubes, sterile 15 and 50 ml;
16. Sucrose solution, 20%, PBS-buffered, sterile; concentration is adjusted in per se known manner with the assistance of a conventional refractometer;
17. Sucrose solutions, 50%, PBS-buffered, sterile; concentration is adjustedin per se known manner with the assistance of a conventional refractometer;
18. Screw-top tubes, sterile;
19. Trypsin solution, "TrypL Express®", from INVITROGEN;
20. Peristaltic pump, from "ismaTec", volumetric flow rate up to 5.8 ml/minute;
21. Refrigerated ultracentrifuge, "Sorvall® Pro 80" with "TH-641" rotor;
22. Ultracentrifuge tubes, sterile, capacity 11 ml, dimensions 9×90 mm;
23. Dilution blocks, 96 wells each of 1.0 ml;
24. MA-104 cells: supplied by FLI;
25. PK-15 cells: supplied by DARD;
26. SK-6 cells: supplied by FLI;
27. SPEV cells: supplied by FLI;
28. Cell suspensions of the SK 6, SPEV and PK-15 cells to be tested with 200,000 cells/ml in cell culture medium with 10% FCS; and
29. Sterile Falcon microtubes, capacity 15 ml.

Example 1

Investigation of the Negative Effect of Pancreatin on Various Cell Lines

For the purposes of detecting viruses in material test samples using cell cultures, the negative effect of the pancreatin sample under investigation on the cells should be ascertained so that false negative results can be eliminated when evaluating CPEs. As stated below, investigations to ascertain the negative effect of a pancreatin test sample suspension were carried out on various cell lines.

0.5 ml portions of a PAN suspension as described above were taken for testing the negative effect and designated "pancreatin suspension test sample".

Low-speed centrifugation: The remaining PAN suspension was centrifuged for 15 minutes at 4,000 rpm (2,700×g) and 4° C. in a refrigerated centrifuge (Megafugee ®1.0R Heraeus SEPATECH® with swinging-bucket rotor no. 2704). After low-speed centrifugation, the supernatant was then centrifuged for a further 15 minutes at 4,000 rpm and 4° C. and designated "supernatant after low-speed centrifugation" to be used for virus titration and ultracentrifugation. The sediment resulting from both low-speed centrifugations were combined (together 1 ml), resuspended in 9 ml of the respective cell culture medium and designated "sediment".

Ultracentrifugation: 5.0 ml were taken from the test sample "supernatant after low-speed centrifugation" and subjected to ultracentrifugation. In preparation for ultracentrifugation, 0.5 ml of 50% sucrose solution was introduced into the ultracentrifugation tube with a pipette. With the ultracentrifuge tube held at an oblique angle, 4.5 ml of 20% sucrose solution was carefully placed on top of the 50% sucrose layer with a dividing layer being discernible between the two solutions. A 5.0 ml layer of the "supernatant after low-speed centrifugation" was then carefully placed on top of the 20% sucrose solution to avoid turbulence and intermixing. The ultracentrifuge tubes were then placed in the ultracentrifuge rotor. The two ultracentrifuge tubes were placed on opposite sides of the rotor and counterbalanced with ultracentrifugation tubes containing PBS. Upon insertion into the rotor, the test samples were centrifuged for 4 hours at 10° C. and 40,000 rpm (273,799×g). After ultracentrifugation, the tubes were removed from the holders on a sterile workbench and marked at 1.5 cm from the bottom of the ultracentrifuge tube. Using a peristaltic pump with the tubing and capillaries that had been previously sterilized, the liquid above the mark was aspirated from the ultracentrifuge tube at a rate of 2 ml/minute with the capillary being located at the upper border of the liquid. The first fraction obtained in this manner was designated "upper fraction after ultracentrifugation." The "lower fraction after ultracentrifugation" (1.5 ml) remaining in the ultracentrifuge tube was removed from the ultracentrifuge tube with the assistance of a single channel pipette. Any sediment remaining on the bottom of the ultracentrifuge tube was resuspended by repeatedly being drawn up with the single channel pipette and likewise removed. The volume of the "lower fraction after ultracentrifugation" was increased to 5.0 ml to correspond with the original virus-containing test sample volume in a sterile graduated tube using the respective cell culture medium. The two resultant fractions were stored at 4° C. or, in the case of extended storage, at −20° C. until further processing.

The samples labeled "pancreatin suspension test sample", "supernatant after low-speed centrifugation", "sediment" (after low-speed centrifugation), "upper fraction after ultracentrifugation" and "lower fraction after ultracentrifugation" (after being made up to 5.0 ml) were then tested for any negative effect on various cell lines. To achieve this, a series of dilutions of the test samples were produced. All the test samples were further diluted by a factor of two from a dilution of 1:5 with the respective cell culture medium. In eight parallel microtiter plates, 100 µl portions of cell suspension comprising PK-15, SPEV or SK 6 cells were added to each well. Also added to each well was 100 µl of the test sample dilutions. When MA 104 cells were tested, microtiter plates with a 24-hour old cell layer were used. The cell culture medium was removed from the wells and replaced with 100 µl of fresh cell culture medium without serum to yield the final test sample dilutions of 1:10, 1:20, 1:40, 1:80, 1:160 etc. As a control, 100 µl of cell culture medium were introduced into eight wells of each microtiter plate instead of 100 µl of the dilution series. Pairs of plates together with a tube containing 4 ml of Pardee buffer and filter paper were placed in air-tight pouches and tightly sealed. The plates were then incubated at 36±1° C. for up to 7 days. Over the period of incubation, the plates were inspected daily by microscope for the extent of CPE, i.e. for cell lysis and/or degeneration of the cells and for the absence of the formation of a cell layer as a result of the negative effect of the pancreatin. The final evaluation was carried out after seven days. The titration was repeated if cell degeneration had already occurred in the controls on the final reading.

Table 1 below shows the results of testing the various samples for their harmful effect on various cell lines. If a test sample was harmful down to the final dilution of, for example, 1:640 but no longer harmful at a dilution of 1:1280, then the result stated for this sample in the Table is "test sample harmful ≥1:640, but <1:1280."

TABLE 1

Test results of pancreatin suspensions and the subfractions thereof for harmfulness towards various cell lines

| Test samples | Cell lines | | | |
|---|---|---|---|---|
| | PK-15 | MA-104 | SK 6 | SPEV |
| | Test samples harmful down to a dilution of: | | | |
| Pancreatin suspension test sample | ≥1:640 <1:1280 | ≥1:160 <1:320 | ≥1:320 <1:640 | ≥1:320 <1:640 |
| Supernatant after low-speed centrifugation | ≥1:640 <1:1280 | ≥1:160 <1:320 | ≥1:320 <1:640 | ≥1:320 <1:640 |
| Sediment | ≥1:160 <1:320 | ≥1:80 <1:160 | ≥1:80 <1:160 | ≥1:40 <1:80 |
| Upper fraction after ultracentrifugation | ≥1:320 <1:640 | ≥1:160 <1:320 | ≥1:320 <1:640 | ≥1:320 <1:640 |
| Lower fraction after ultracentrifugation | ≥1:40 <1:80 | ≥1:20 <1:40 | ≥1:20 <1:40 | ≥1:20 <1:40 |

From the results shown in Table 1, it is clear that in the "lower fraction after ultracentrifugation" which has been subjected to an ultracentrifugation step as previously described and in which the infectious virus load has been concentrated, there is a considerable reduction in the harmful effect towards the investigated cell lines relative to the other test samples investigated.

If the harmful effect of the untreated pancreatin suspension test sample is compared with the lower fractions after ultracentrifugation, it has been possible in the above-described test for MA-104 cells to reduce the harmful effect by a factor of 8 and by a factor of 16 in each of the other three cell lines tested. The supernatant was still slightly turbid after the pancreatin suspension test sample had been twice subjected to low-speed centrifugation. During ultracentrifugation, these insoluble particles settle as a thin deposit on the bottom of the ultracentrifuge tube. This deposit was resuspended and was a constituent of the "lower fraction after ultracentrifugation". Thus, it may be assumed that this deposit contributes to the residual harmful effect of the "lower fraction after ultracentrifugation" and that its effect may be further reduced by separating and not resuspending this deposit.

Example 2

Investigation of Pancreatin Samples with an Elevated Virus Titer

The aim of investigating pancreatin samples with the addition of an elevated virus titer ("high-spike tests") was inter alia to show that the process described herein is suitable for quantitatively separating the viral load from the pancreatin sample and its constituents which may be harmful to living cells. High-titer "spiked virus preparations" of each of the viruses to be investigated were prepared. "High-titer" means a titer of the spiked virus preparation of at least 4 steps of the base-ten logarithm (log) of the semimaximal "Tissue Culture Infectious Dose" per ml of the investigated test sample ($TCID_{50}$/ml). High-titer spiked virus preparations of PCV may, for example, be obtained in accordance with the method of I. Tischer et al., Arch. Virol. 96 (1987) 39-57, by pretreating the PK-15 cells used for culturing with D-(+)-glucosamine solution.

a. High-Spike Test with EMCV (Strain LC 75)

0.75 ml of a high-titer (7.70±0.10 log $TCID_{50}$/ml) spiked virus preparation of EMCV (strain LC 75) and 0.75 ml of antibiotic solution were added to a PAN suspension (produced by addition of 4.5 ml of Dulbecco medium to 0.75 g of pancreatin and stirring for 50 minutes in an ice bath) and the resultant suspension was stirred for a further 10 minutes. 0.5 ml of this suspension was taken for virus titration and stored at 4° C. until titration ("EMCV high fraction 1"). The remaining suspension was centrifuged for 15 minutes at 4,000 rpm (2,700×g) and 4° C. The supernatant after centrifugation was recentrifuged in a new centrifuge tube for 15 minutes at 4° C. and 4,000 rpm. The supernatant after the second centrifugation was quantitatively transferred into a sterile tube ("EMCV high fraction 2"). The two sediments after low-speed centrifugation were resuspended with a total of 6.5 ml of Dulbecco medium, combined and recentrifuged for 15 minutes at 4,000 rpm and 4° C. The resultant supernatant was transferred into a sterile tube. The sediment was washed twice with a 6.5 ml portion of fresh Dulbecco medium. The three washing solutions were combined and used for the virus titration ("EMCV high fraction 3"). After three washings, the sediment was resuspended in 6.5 ml of Dulbecco medium and then titrated ("EMCV high fraction 4").

5.0 ml of EMCV high fraction 2 were subjected to ultracentrifugation in the discontinuous sucrose gradient as described in Example 1. After ultracentrifugation, the upper ("EMCV high fraction 5") and lower ("EMCV high fraction 6") fractions were obtained separately and titrated.

Diluting by a factor of three, a series of viral dilutions were produced and each transferred each with 12 dilution steps in 12 parallels onto microtiter plates with SPEV cell suspension. Spike virus—titration from a dilution of $10^{-3}$; EMCV high fraction 1—titration from a dilution of $10^{-2}$; EMCV high fraction 2—titration from a dilution of $10^{-2}$; EMCV high fraction 4—titration form a dilution of $10^{-1}$; EMCV high fraction 3—titration from a dilution of $10^{-2}$; EMCV high fraction 5—titration from an undiluted test sample; EMCV high fraction 6—triplicate titration from a dilution of $10^{-3}$. The microtiter plates were incubated at 36±1° C. in an atmosphere comprising approximately 5% $CO_2$ and, over the course of 6-7 days, evaluated by microscope for the development of CPE in the wells. Titer levels were calculated in accordance with the Spearman-Kärber method. The results of the high-spike test with EMCV are shown in Table 2 below.

TABLE 2

Results of the high-spike tests with EMCV in pancreatin suspensions

| Test sample | Titer log $TCID_{50}$/ml[1] | Test sample volume [ml] | Virus load [log $TCID_{50}$/ml + log volume][2] |
|---|---|---|---|
| Spike virus (EMCV) | 7.70 ± 0.10 | 0.75 | 7.58 ± 0.20 |
| EMCV high fraction 1 | 7.14 ± 0.10 | 7.5 | 8.02 ± 0.20 |
| EMCV high fraction 2 | 7.38 ± 0.09 | 5 | 8.08 ± 0.18 |
| EMCV high fraction 4 | 3.32 ± 0.08 | 7.5 | 4.20 ± 0.16 |

TABLE 2-continued

Results of the high-spike tests with EMCV in pancreatin suspensions

| Test sample | Titer log $TCID_{50}$/ml[1] | Test sample volume [ml] | Virus load [log $TCID_{50}$/ml + log volume][2] |
|---|---|---|---|
| EMCV high fraction 3 | 5.67 ± 0.10 | 19.5 | 6.96 ± 0.20 |
| EMCV high fraction 5 | 4.71 ± 0.10 | 8.5 | 5.64 ± 0.20 |
| EMCV high fraction 6 (1) | 6.99 ± 0.11 | 5 | 7.69 ± 0.22 |
| EMCV high fraction 6 (2) | 7.07 ± 0.10 | 5 | 7.77 ± 0.20 |
| EMCV high fraction 6 (3) | 6.99 ± 0.10 | 5 | 7.69 ± 0.20 |
| Average of the 3 fractions for EMCV high fraction 6[3] | 7.02 ± 0.05[3] | 5 | 7.72 ± 0.10 |

[1]Value is the standard deviation of the individual titration;
[2]Value is the 95% confidence interval;
[3]Value is the standard deviation of 3 determinations From Table 2 it is clear that when the process described herein is carried out, the viral load of the untreated spiked test samples (EMCV high fractions 1 and 2), taking into account the generally accepted range of variation of 0.5 log steps, was approximately quantitatively recovered in the lower fraction after ultracentrifugation (EMCV high fraction 6). It may furthermore be concluded from the test results that the pancreatin sample itself had no inhibiting or inactivating effect on EMCV.

b. High-Spike Test with Porcine Parvovirus

Porcine parvovirus (PPV) can be cultured with SK 6 cells and concentrated after cultivation if the virus yield is too low.

1.0 ml of a high-titer (4.75±0.06 log $TCID_{50}$/ml) spiked virus preparation of PPV was added to a PAN suspension (produced by addition of 7.0 ml of Dulbecco medium and stirring for 50 minutes in an ice bath) and the resultant suspension was stirred for an additional 10 minutes. 0.5 ml of this suspension was taken for virus titration and stored at 4° C. until titration ("PPV high fraction 1"). The remaining suspension was centrifuged for 15 minutes at 4,000 rpm (2,700×g) and 4° C. The supernatant after centrifugation was recentrifuged in a new centrifuge tube for 15 minutes at 4° C. and 4,000 rpm. The supernatant after the second centrifugation was quantitatively transferred into a sterile tube ("PPV high fraction 2"). After low-speed centrifugation, the two sediments were resuspended with a total of 9 ml of Dulbecco medium, combined and recentrifuged for 15 minutes at 4,000 rpm and 4° C. The resultant supernatant was transferred into a sterile tube. The sediment was washed twice with a 9 ml portion of fresh Dulbecco medium. The three washing solutions were then combined and used for the virus titration ("PPV high fraction 3"). After three washings, the sediment was resuspended in 9 ml of Dulbecco medium and then titrated ("PPV high fraction 4").

5.0 ml of PPV high fraction 2 were subjected to ultracentrifugation in the discontinuous sucrose gradient as previously described in Example 1. After ultracentrifugation, the upper ("PPV high fraction 5") and lower ("PPV high fraction 6") fractions were obtained separately and titrated.

Diluting by a factor of three, a series of viral dilutions were produced and each transferred with 12 dilution steps in 12 parallels onto microtiter plates with SK 6 cell suspension. The microtiter plates were incubated at 36±1° C. in an atmosphere comprising approximately 5% $CO_2$ and, over the course of 6-7 days, evaluated by microscope for the development of CPE in the wells. After this incubation period, the plates were fixed by the addition of an ice-cold acetone/methanol mixture. The wells with uncertain CPE were incubated for the final titer determination with FITC-labeled anti-PPV antibody and then evaluated under a UV light microscope. Titer levels were calculated in accordance with the Spearman-Kärber method.

TABLE 3

Results of the high-spike tests with PPV in pancreatin suspensions

| Test sample | Titer log $TCID_{50}/ml^{1)}$ | Test sample volume [ml] | Virus load [log $TCID_{50}/ml$ + log volume]$^{2)}$ |
|---|---|---|---|
| Spike virus (PPV) | 4.95 ± 0.15 | 1 | 4.95 ± 0.30 |
| PPV high fraction 1 | 3.56 ± 0.08 | 10 | 4.56 ± 0.16 |
| PPV high fraction 2 | 4.47 ± 0.08 | 5 | 5.17 ± 0.16 |
| PPV high fraction 4 | 2.08 ± 0.11 | 10 | 3.08 ± 0.22 |
| PPV high fraction 3 | 2.38 ± 0.09 | 27 | 3.81 ± 0.18 |
| PPV high fraction 5 | <3.15 | 8.5 | <4.08 |
| PPV high fraction 6 (1) | 4.67 ± 0 | 5 | 5.37 ± 0 |
| PPV high fraction 6 (2) | 4.43 ± 0.08 | 5 | 5.13 ± 0.16 |
| PPV high fraction 6 (3) | 4.47 ± 0.08 | 5 | 5.17 ± 0.16 |
| Average of the 3 fractions for PPV high fraction 6$^{3)}$ | 4.52 ± 0.13$^{3)}$ | 5 | 5.22 ± 0.26 |

$^{1)}$Value is the standard deviation of the individual titration;
$^{2)}$Value is the 95% confidence interval;
$^{3)}$Value is the standard deviation of 3 determinations From Table 3 it is clear that in the EMCV high spike experiment, if the process described herein is successful, the viral load of the untreated spiked test samples (PPV high fractions 1 and 2), taking into account the generally accepted range of variation of 0.5 log steps, is approximately quantitatively recovered in the lower fraction after ultracentrifugation (PPV high fraction 6). In the PPV high fraction 1 (i.e. in the presence of insoluble particles), a titer value one log-step lower than the PPV high fraction 2 is shown. The presence of insoluble constituents thus apparently disrupts titration. Furthermore, it may be concluded from the test results that the pancreatin sample itself had no inhibiting or inactivating effect on PPV.

Example 3

Investigation of Pancreatin Samples with the Addition of a Low Virus Titer

The aim of investigating pancreatin samples with the addition of decreasing virus titers ("low-spike tests") was inter alia to ascertain the limit of detection of the process described herein. Quantitative detection of the viral load in the individual test samples with a decreasing virus titer is considered to be successful if the virus titer of the originally added spiked virus preparation, taking into account the generally accepted range of variation of 0.5 log steps, is approximately quantitatively recovered in the lower fractions after ultracentrifugation.

a. Low-Spike Test with EMCV

A PAN suspension was produced (with 2.5 g of porcine pancreatin, 2.5 ml of antibiotic solution and 20 ml of Dulbecco medium). The low-spike test was then carried out in duplicate in mutually independent tests.

In the first test, the batches described below were produced from PAN suspension plus EMCV spike virus solution:

(1) 4.5 ml of pancreatin suspension+0.5 ml of $10^{-3}$ dilution of spike virus; resultant dilution $10^{-4}$;
(2) 4.5 ml of pancreatin suspension+0.5 ml of $10^{-4}$ dilution of spike virus; resultant dilution $10^{-5}$;
(3) 4.5 ml of pancreatin suspension+0.5 ml of $10^{-5}$ dilution of spike virus; resultant dilution $10^{-6}$;
(4) 4.5 ml of pancreatin suspension+0.5 ml of $10^{-6}$ dilution of spike virus; resultant dilution $10^{-7}$;
(5) 4.5 ml of pancreatin suspension+0.5 ml of $10^{-7}$ dilution of spike virus; resultant dilution $10^{-8}$; and
(6) 4.5 ml of pancreatin suspension+0.5 ml of $10^{-8}$ dilution of spike virus; resultant dilution $10^{-9}$.

All the batches were incubated for one hour at room temperature and then subjected to low-speed centrifugation for 15 minutes at 4° C. and 4,000 rpm (2,700×g). The supernatants after low-speed centrifugation were transferred into fresh centrifuge tubes and subjected to another low-speed centrifugation under the same conditions. The volume of the supernatants after the low-speed centrifugations were increased to 5.0 ml with the addition of cell culture medium and, after low-speed centrifugation, the supernatants were subjected to ultracentrifugation in the discontinuous sucrose gradient as previously described in Example 1. After ultracentrifugation, the upper fractions ("EMCV low fraction 2"; down to 1.5 cm of the ultracentrifuge tube) were removed with a peristaltic pump and the respective lower fractions ("EMCV low fraction 3") were removed from the ultracentrifuge tube with a pipette. After ultracentrifugation, the volume of the lower fractions were increased to 5.0 ml with MEM and then used for the titrations or culturing in tissue culture flasks.

Diluting by a factor of three, a series of viral dilutions were then produced from each of batches (1), (2) and (3) described above and each transferred with 12 dilution steps in 12 parallels onto microtiter plates with SPEV cell suspension (100 µl portion per well of freshly prepared cell suspension of SPEV cells with 200,000 cells/ml). The test samples of the EMCV low fraction 3 of all batches were also transferred into cell culture flasks with a base area of 25 cm$^2$ and 10 ml portions of freshly prepared cell suspension of SPEV cells having 200,000 cells/ml. Six tissue culture flasks for each test sample were infected with a 0.2 ml portion of the test sample EMCV low fraction 3. In parallel, a control was provided by one tissue culture flask without any addition. All the titration plates and tissue culture flasks were incubated at 36±1° C. and, over the course of 6-7 days, evaluated by microscope for the development of CPE in the wells or tissue culture flasks. The titer level was calculated in the titrated test samples in accordance with the Spearman-Kärber method.

If no CPE was observed in any of the six tissue culture flasks of a batch after 7 days, the flasks were frozen at −70° C. and thawed three times. The entire contents of the tissue culture flasks were combined and filtered through a 0.1 µm (pore size) filter. The resulting filtrate was used to prepare a second pass on SPEV cell suspension: 2 tissue culture flasks each comprising 10 ml of fresh SPEV cell suspension were infected with 2 ml of the suspension obtained from the first pass and likewise incubated for up to 7 days at 36±1° C. and observed for the development of CPE. If no CPE was observed in the second pass, a third pass was carried out. If a negative result was also found after the third pass, the original test sample was deemed to be free of EMCV.

A detection limit of the process described herein of one infectious unit of EMCV per 0.1 g of pancreatin sample used was determined in the above-stated low-spike tests with graduated dilutions of EMCV.

b. Low-Spike Test with PPV

A PAN suspension was produced (with 2.5 g of porcine pancreatin, 2.5 ml of antibiotic solution and 20 ml of Dulbecco medium). The low-spike test was then carried out in duplicate in mutually independent tests.

The batches described below were produced from PAN suspension plus PPV spike virus solution:
(7) 4.5 ml of pancreatin suspension+0.5 ml of $10^{-1}$ dilution of spike virus;
(8) 4.5 ml of pancreatin suspension+0.5 ml of $10^{-2}$ dilution of spike virus;
(9) 4.5 ml of pancreatin suspension+0.5 ml of $10^{-3}$ dilution of spike virus;
(10) 4.5 ml of pancreatin suspension+0.5 ml of $10^{-4}$ dilution of spike virus;

All batches were incubated for one hour at room temperature and then subjected to low-speed centrifugation for 15 minutes at 4° C. and 4,000 rpm (2,700×g). After low-speed centrifugation, the supernatants were transferred into fresh centrifuge tubes and subjected to another low-speed centrifugation under the same conditions. The volume of the supernatants after the low-speed centrifugations were increased to 5.0 ml with cell culture medium and the supernatants, after low-speed centrifugation, were subjected to ultracentrifugation in the discontinuous sucrose gradient as previously described in Example 1. After ultracentrifugation, the upper fractions ("PPV low fraction 2"; down to 1.5 cm of the ultracentrifuge tube) were removed with a peristaltic pump and the respective lower fractions ("PPV low fraction 3") were removed from the ultracentrifuge tube with a pipette. After centrifugation, the volume of the lower fractions were increased to 5.0 ml with Dulbecco medium and then used for the titrations or culturing in tissue culture flasks.

Diluting by a factor of three, a series of viral dilutions were then produced from each of batches (7), (8) and (9) described above and each transferred with 12 dilution steps in 8 parallels onto microtiter plates with SK-6 cell suspension (100 µl portion per well of freshly prepared cell suspension of SK-6 cells with 200,000 cells/ml).

Six tissue culture flasks for each of the batches were infected with a 0.2 ml portion of PPV low fraction 3. In parallel, a control was provided by one tissue culture flask without any addition. All the titration plates and tissue culture flasks were incubated at 36±1° C. and, over the course of 6-7 days, evaluated by microscope for the development of CPE in the wells or tissue culture flasks. The titer level was calculated in the titrated test samples in accordance with the Spearman-Kärber method.

If no CPE was observed in any of the six tissue culture flasks of a batch after 7 days, these flasks were frozen at −70° C. and thawed three times. The entire contents of the tissue culture flasks were combined and filtered through a 0.1 µm (pore size) filter. The resulting filtrate was used to prepare a second pass on SK-6 cell suspension: 2 tissue culture flasks each comprising 10 ml of fresh SK-6 cell suspension were infected with 2 ml of the suspension obtained from the first pass and likewise incubated for up to 7 days at 36±1° C. and observed for the development of CPE. If no CPE was observed in the second pass, a third pass was carried out. If no CPE was found in the third pass either, the cell culture medium was removed from the third pass flasks after 7 days and the cell layer was fixed with ice-cold acetone/methanol (80:20 vol./vol.). Infected cells were then detected in the tissue culture flasks by means of FITC-labeled anti-PPV antibody (with 1 ml of antibody solution per flask; incubation for 60 minutes at 37° C., washing with washing buffer and subsequent evaluation by microscope under UV light). If the third pass flasks were free of infected cells, the original test sample was deemed to be free of PPV.

A detection limit of the process described herein of one infectious unit of PPV per 0.1 g of pancreatin sample used was determined in the above-stated low-spike tests with graduated dilutions of PPV.

Pharmaceutical Compositions

Another embodiment of the invention described herein includes a process for manufacturing a pharmaceutical composition comprising pancreatin wherein such pharmaceutical composition can be in a dosage form suitable for oral administration. The oral dosage form can be for immediate and/or modified release, such dosage form can be tablets, microtablets, pellets, micropellets, microspheres, granules, granulates, powders, suspensions, emulsions, dispersions, capsules sachets as well as other dosage forms.

In one embodiment of a process for the manufacturing of a pharmaceutical composition, the pancreatin and/or its dosage form is further coated with a gastric acid resistant coating.

In another embodiment of such process for the manufacture of a pharmaceutical composition, the optionally gastric acid resistant coated pancreatin or its dosage form is further filled into sachets and/or capsules.

A further embodiment described herein are pharmaceutical compositions which can be prepared utilizing the processes described herein. The pharmaceutical compositions can comprise a pharmacologically effective quantity of pancreatin having a viral load, wherein the viral load of the pancreatin has been quantitatively determined by the process comprising the steps of:

i) producing a liquid pancreatin test sample suitable for centrifugation;

ii) low-speed centrifugation of the liquid pancreatin test sample under conditions in which viruses with sedimentation constants of greater than about 120 S do not form a pellet whereby the low-speed centrifugation of the liquid pancreatin test sample yields a supernatant;

iii) ultracentrifugation of the liquid pancreatin test sample supernatant with a discontinuous gradient medium under conditions wherein transfer of the viral load from the liquid pancreatin test sample supernatant into a target fraction of the discontinuous gradient medium is substantially complete;

iv) quantitatively separating the target fraction containing the viral load from the liquid pancreatin test sample supernatant; and v) quantitatively determining the viral load of the pancreatin sample; and b) one or more pharmaceutically acceptable excipients.

The viral load can optionally be reduced as part of manufacturing a pharmaceutical composition as described herein. Methods of reducing viral loads in pancreatin are know to those of ordinary skill in the art.

Formulation Example 1—

Pharmaceutical Composition Comprising Pancreatin

A pharmaceutical composition comprising: 10 kg of pancreatin is mixed with 2.5 kg of ethylene glycol 4000 and 1.5 kg of propan-2-ol to give a mixture which was then extruded in an extruding press. Pancreatin micropellets are prepared as disclosed in EP 0 583 726 and can be further packed into capsules or sachets.

Formulation Example 2—

Pancreatin Micopellets Coated with a Gastric Acid Resistant Coating

The pancreatin micropellets obtained by the preceding example can be provided with a gastric acid resistant coating. For example, the pancreatin micropellets can be coated with gastric-juice-resistant film-forming agents such as, e.g., hydroxypropyl-methylcellulose acetate succinate (HPMCAS), hydroxypropylmethylcellulose phthalate (HPMCP), cellulose acetate phthalate (CAP) or polyvinyl acetate phthalate (PVAP). Copolymers known as film-forming agents such as, for example, methacrylic acid/methyl methacrylate copolymers or methacrylic acid/ethyl acrylate copolymers, can also be used. The film-forming agents can be applied to the pancreatin micropellets using various film-coating apparatus, e.g. coaters, in the customary use forms, e.g. as organic solutions or organic or aqueous dispersions, optionally with addition of a conventional plasticizer. The resulting gastric acid-resistant film-coated pancreatin micropellets are distinguished by a high bulk density, for example in the range from 0.6 g/ml to 0.85 g/ml, which makes it possible to increase the filling weight per capsule and thus the active compound content of each capsule. Further experimental details on the process for preparing the gastric acid-resistant film-coated pancreatin micropellets are disclosed in EP 0 583 726.

Examples of pharmaceutically acceptable excipients include binding agents such as polyethylene glycol 1500, polyethylene glycol 2000, polyethylene glycol 3000, polyethylene glycol 4000, polyethylene glycol 6000, polyethylene glycol 8000, polyethylene glycol 10000, hydroxypropyl methylcellulose, polyoxyethylen, copolymers of polyoxyethylen-polyoxypropylen and mixtures of said organic polymers. The foregoing list of pharmaceutically acceptable binding agents is not meant to be exhaustive, but merely illustrative as a person of ordinary skill in the art would understand that many other pharmaceutically acceptable binding agents or combination of binding agents could also be used. Polyethylene glycol 4000 is the preferred pharmaceutically acceptable binding agent.

Examples of additional pharmaceutically acceptable excipients include gliding agents like magnesium stearate or calcium stearate, stearic acid, talcum and/or starch; fillers like calcium phosphate, corn starch, dextrans, dextrin, hydrated silicon dioxide, microcrystalline cellulose, kaolin, lactose, mannitol, polyvinyl pyrrolidone, precipitated calcium carbonate, sorbitol and/or talcum; disintegrating agents like Aerosil™ (silicic acid), alginic acid, amylose, calcium alginate, calcium carbonate, formaldehyde gelatin, pectic carbonate, sago starch, sodium bicarbonate and/or starch; and/or moisturizers like glycerol and/or starch. The foregoing list of pharmaceutically acceptable excipients is not meant to be exhaustive, but merely illustrative as a person or ordinary skill in the art would understand that many other pharmaceutically acceptable excipients or combination of excipients could also be used.

Methods of Treat Pancreatine Exocrine Insufficiency

Maldigestion in mammals such as humans is usually based on a deficiency of digestive enzymes, in particular on a deficiency of endogenous lipase, but also of protease and/or amylase. The cause of such a deficiency of digestive enzymes is frequently a hypofunction of the pancreas (e.g. pancreatic insufficiency, usually known as pancreatic exocrine insufficiency), the organ which produces the largest quantity of, and the most important, endogenous digestive enzymes. If the pancreatic insufficiency is pathological, it may be congenital or acquired. Acquired chronic pancreatic insufficiency may, for example, result from alcoholism. Congenital pancreatic insufficiency may, for example, result from disease such as cystic fibrosis. The consequences of the deficiency of digestive enzymes may be severe symptoms of under-nutrition and malnutrition, which may be accompanied by increased susceptibility to secondary illnesses. One embodiment is a method of treating pancreatin exocrine insufficiency of any origin in a mammalian subject comprising the step of administering the pharmaceutical compositions described herein.

In yet another embodiment, a method is provided for the treatment of a medical condition such as digestive disorders, pancreatic exocrine insufficiency, pancreatitis, cystic fibrosis, diabetes type I and/or diabetes type II by administering a therapeutically effective amount of pancreatin to a person in need of such treatment.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar references in the context of this disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., such as, preferred, preferably) provided herein, is intended merely to further illustrate the content of the disclosure and does not pose a limitation on the scope of the claims. No language in the specification should be construed as indicating any non-claimed element as essential to the practice of the present disclosure.

Alternative embodiments of the claimed disclosure are described herein, including the best mode known to the inventors for practicing the claimed invention. Of these, variations of the disclosed embodiments will become apparent to those of ordinary skill in the art upon reading the foregoing disclosure. The inventors expect skilled artisans to employ such variations as appropriate (e.g., altering or combining features or embodiments), and the inventors intend for the invention to be practiced otherwise than as specifically described herein.

Accordingly, this invention includes all modifications and equivalents of the subject matter recited in the claims appended hereto as permitted by applicable law. Moreover, any combination of the above described elements in all possible variations thereof is encompassed by the invention unless otherwise indicated herein or otherwise clearly contradicted by context.

The use of individual numerical values are stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Thus, as a general matter, "about" or "approximately" broaden the numerical value. Also, the disclosure of ranges is intended as a continuous range including every value between the minimum and maximum values plus the broadening of the range afforded by the use of the term "about" or "approximately." Thus, recitation of ranges of values herein are merely intended to serve as a shorthand method of referring individually to each separate value falling within the range, unless otherwise indicated herein, and each separate value is incorporated into the specification as if it were individually recited herein.

It is to be understood that any ranges, ratios and ranges of ratios that can be formed by, or derived from, any of the data disclosed herein represent further embodiments of the present disclosure and are included as part of the disclosure as though they were explicitly set forth. This includes ranges that can be formed that do or do not include a finite upper and/or lower boundary. Accordingly, a person of ordinary skill in the art most closely related to a particular range, ratio or range of ratios will appreciate that such values are unambiguously derivable from the data presented herein.

The invention claimed is:

1. A process for manufacturing a pharmaceutical composition comprising pancreatin, comprising the steps of:

(a) producing a liquid pancreatin test sample from a quantity of pancreatin, the liquid pancreatin test sample comprising pancreatin, a cell culture medium suitable for cell line used to culture virus, and one or more antibiotics;

(b) centrifugation of the liquid pancreatin test sample at a relative centrifugal force of less than 10,000×g, in which viruses with sedimentation constants of greater than about 120 S do not form a pellet whereby the low-speed centrifugation of the liquid pancreatin test sample produces a supernatant;

(c) ultracentrifugation of the liquid pancreatin test sample supernatant with a discontinuous gradient medium at a relative centrifugal force greater than 100,000×g transfer a virus from the liquid pancreatin test sample supernatant into a target fraction of the discontinuous gradient medium, whereby the target fraction is quantitatively separated from the liquid pancreatin test sample supernatant;

(d) quantitatively determining a viral load of the pancreatin test sample by culturing the target fraction with a population of cells, assessing the population of cells for viral infection, and calculating a viral titer in the target traction; and (e) producing a dosage form suitable for oral administration from the quantity of pancreatin when the liquid pancreatin test sample is determined to be substantially free of virus;

wherein steps (a), (b), and (c) are performed without altering the viral load.

2. The process of claim 1, wherein the target fraction is filtered through a micro filter before quantitatively determining the viral load.

3. The process of claim 1, wherein the liquid pancreatin test sample suspension is at a temperature of between about 0° C. and about 15° C. during low-speed centrifugation.

4. The process of claim 1, wherein the centrifugation of step (b) is at a relative centrifugal force between about 1,500×g and about 5,000×g.

5. The process of claim 1, wherein the centrifugation of step (b) is carried out for longer than five minutes.

6. The process of claim 1, wherein ultracentrifugation is carded out for a duration of more than one hour.

7. The process of claim 1, wherein the ultracentrifugation is carried out for a duration of between about 2 hours and about 8 hours and the relative centrifugal force is between about 200,000×g and about 350,000×g.

8. The process of claim 1, wherein the liquid pancreatin test sample is at a temperature of between about 0° C. and about 15° C. during ultracentrifugation.

9. A process for manufacturing a pharmaceutical composition containing pancreatin, comprising (a) providing or obtaining a pancreatin test sample from a quantity of pancreatin, wherein the pancreatin test sample further comprises a cell culture medium suitable for a cell line used to culture virus, (b) isolating a target fraction of the test sample in which transfer of a virus into the target fraction is substantially complete; wherein the isolating step comprises (i) centrifugation of the pancreatin test sample at a relative centrifugal force of less than 10,000×g to produce a pancreatin test sample supernatant, in which viruses with sedimentation constants of greater than about 120 S do not form a pellet: and (ii) ultracentrifugation of the pancreatin test sample supernatant with a discontinuous gradient medium at a relative centrifugal force greater than 100,000×g, whereby the target fraction is quantitatively separated from the pancreatin test sample supernatant;

(c) quantitatively determining a viral load of the pancreatin test sample by culturing the target fraction with a population of cells, assessing the population of cells for viral infection, and calculating a viral titer in the target fraction, and (d) processing at least a portion of the quantity of pancreatin to obtain the pharmaceutical composition when the pancreatin test sample is determined to be substantially free of virus;

wherein steps (a) and (b) are performed without altering a viral load.

10. The process of claim 9, wherein the processing step comprises combining the quantity of pancreatin with one or more pharmaceutically acceptable excipients.

11. The process of claim 9, wherein the processing step comprises preparing pancreatin micropellets.

12. The process of claim 11, further comprising coating the pancreatin micropellets with a gastric acid resistant coating.

13. The process of claim 12, wherein the gastric acid resistant coating is hydroxypropyl-methylcellulose acetate succinate (HPMCAS), hydroxypropylmethytceltulose phthalate (HPMCP), cellulose acetate phthalate (CAP) or polyvinyl acetate phthalate (PVAP).

14. The process of claim 12, wherein the gastric acid resistant coating is hydroxypropylmethylcaulose phthalate (HPMCP).

* * * * *